(12) United States Patent
Freier

(10) Patent No.: US 7,754,698 B2
(45) Date of Patent: Jul. 13, 2010

(54) MODULATION OF FR-ALPHA EXPRESSION

(75) Inventor: Susan M. Freier, San Diego, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 26 days.

(21) Appl. No.: 11/971,027

(22) Filed: Jan. 8, 2008

(65) Prior Publication Data

US 2008/0167265 A1 Jul. 10, 2008

Related U.S. Application Data

(60) Provisional application No. 60/884,121, filed on Jan. 9, 2007.

(51) Int. Cl.
*A61K 31/70* (2006.01)
*C07H 21/02* (2006.01)
*C12Q 1/68* (2006.01)
*C12N 5/00* (2006.01)

(52) U.S. Cl. .................. 514/44; 536/23.1; 536/24.1; 536/24.5; 435/6; 435/375; 435/377

(58) Field of Classification Search ................ None
See application file for complete search history.

(56) References Cited

U.S. PATENT DOCUMENTS

| | | | |
|---|---|---|---|
| 5,801,154 A | | 9/1998 | Baracchini et al. |
| 6,582,908 B2 | | 6/2003 | Fodor et al. |
| 7,030,236 B2 * | | 4/2006 | Jhaveri et al. ............ 536/24.5 |
| 2001/0053519 A1 | | 12/2001 | Fodor et al. |
| 2003/0228597 A1 | | 12/2003 | Cowsert et al. |
| 2004/0259247 A1 * | | 12/2004 | Tuschl et al. ................ 435/375 |
| 2007/0031844 A1 * | | 2/2007 | Khvorova et al. ............ 435/6 |

OTHER PUBLICATIONS

Branch et al., "A good antisense molecule is hard to find," TIBS (1998) 23:45-50.
Chan et al., "Folate Receptor-alpha Is a Cofactor for Cellular Entry by Marburg and Ebola Viruses" Cell (2001) 106:117-126.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Crooke et al., "Basic Principles of Antisense Therapeutics" Antisense Research and Application (1998) Chapter 1:1-50.
Elwood, "Molecular Cloning and Characterization of the Human Folate-binding Protein cDNA from Placenta and Malignant Tissue Culture (KB) Cells" J. Biol. Chem. (1989) 264:14893-14901.
Lacey et al., "Complementary DNA for the Folate Binding Protein Correctly Predicts Anchoring to the Membrane by Glycosyl-Phosphatidylinositol" J. Clin. Invest. (1989) 84:715-720.
New England Biolabs 1998/99 Catalog (cover page and pp. 121 and 284).
Reynolds et al., "Rational siRNA design for RNA interference" Nature Biotechnology (2004) 22(3):326-330.
Sanghvi et al., "Heterocyclic Base Modifications in Nucleic Acids and Their Applications in Antisense Oligonucleotides" Antisense Research and Applications (1993) pp. 273-288.

* cited by examiner

*Primary Examiner*—Sean R McGarry
(74) *Attorney, Agent, or Firm*—Iris Pharmaceuticals, Inc. Patent Dept.

(57) ABSTRACT

Disclosed herein are compounds, compositions and methods for modulating the expression of FR-alpha in a cell, tissue or animal. Also provided are methods of target validation. Also provided are uses of disclosed compounds and compositions in the manufacture of a medicament for treatment of diseases and disorders.

40 Claims, No Drawings

SEQUENCE LISTING

<160> NUMBER OF SEQ ID NOS: 104

<210> SEQ ID NO 1
<211> LENGTH: 944
<212> TYPE: DNA
<213> ORGANISM: H. Sapiens

<400> SEQUENCE: 1

| | | | | | |
|---|---|---|---|---|---|
| tcaagattaa | acgacaagga | cagacatggc | tcagcggatg | acaacacagc tgctgctcct | 60 |
| tctagtgtgg | gtggctgtag | taggggaggc | tcagacaagg | attgcatggg ccaggactga | 120 |
| gcttctcaat | gtctgcatga | acgccaagca | ccacaaggaa | agccaggcc ccgaggacaa | 180 |
| gttgcatgag | cagtgtcgac | cctggaggaa | gaatgcctgc | tgttctacca acaccagcca | 240 |
| ggaagcccat | aaggatgttt | cctacctata | tagattcaac | tggaaccact gtggagagat | 300 |
| ggcacctgcc | tgcaaacggc | atttcatcca | ggacacctgc | ctctacgagt gctcccccaa | 360 |
| cttggggccc | tggatccagc | aggtggatca | gagctggcgc | aaagagcggg tactgaacgt | 420 |
| gcccctgtgc | aaagaggact | gtgagcaatg | gtgggaagat | gtcgcacct cctacacctg | 480 |
| caagagcaac | tggcacaagg | gctggaactg | gacttcaggg | tttaacaagt gcgcagtggg | 540 |
| agctgcctgc | aacctttcc | atttctactt | ccccacaccc | actgttctgt gcaatgaaat | 600 |
| ctggactcac | tcctacaagg | tcagcaacta | cagccgaggg | agtggccgct gcatccagat | 660 |
| gtggttcgac | ccagcccagg | gcaaccccaa | tgaggaggtg | gcgaggttct atgctgcagc | 720 |
| catgagtggg | gctgggccct | gggcagcctg | gccttcctg | cttagcctgg ccctaatgct | 780 |
| gctgtggctg | ctcagctgac | ctcctttac | cttctgatac | ctggaaatcc ctgccctgtt | 840 |
| cagccccaca | gctcccaact | atttggttcc | tgctccatgg | tcgggcctct gacagccact | 900 |
| ttgaataaac | cagacaccgc | acatgtgtct | tgagaattat | ttgg | 944 |

<210> SEQ ID NO 2
<211> LENGTH: 1032
<212> TYPE: DNA
<213> ORGANISM: H. Sapiens

<400> SEQUENCE: 2

| | | | | | |
|---|---|---|---|---|---|
| ggcaaggggg | agtgtagagc | agagcagaag | cctgagccag | acggagagcc acctcctctc | 60 |
| ccaggaactg | aacccaaagg | atcacctggt | attccctgag | agtacagatt tctccggcgt | 120 |
| ggccctcaag | ggacagacat | ggctcagcgg | atgacaacac | agctgctgct ccttctagtg | 180 |
| tgggtggctg | tagtagggga | ggctcagaca | aggattgcat | gggccaggac tgagcttctc | 240 |
| aatgtctgca | tgaacgccaa | gcaccacaag | gaaaagccag | gccccgagga caagttgcat | 300 |
| gagcagtgtc | gaccctggag | gaagaatgcc | tgctgttcta | ccaacaccag ccaggaagcc | 360 |
| cataaggatg | tttcctacct | atatagattc | aactggaacc | actgtggaga tggcacct | 420 |
| gcctgcaaac | ggcatttcat | ccaggacacc | tgcctctacg | agtgctcccc caacttgggg | 480 |
| ccctggatcc | agcaggtgga | tcagagctgg | cgcaaagagc | gggtactgaa cgtgcccctg | 540 |
| tgcaaagagg | actgtgagca | atggtgggaa | gattgtcgca | cctcctacac ctgcaagagc | 600 |
| aactggcaca | agggctggaa | ctggacttca | gggtttaaca | agtgcgcagt gggagctgcc | 660 |
| tgccaacctt | tccatttcta | cttccccaca | cccactgttc | tgtgcaatga aatctggact | 720 |
| cactcctaca | aggtcagcaa | ctacagccga | gggagtggcc | gctgcatcca gatgtggttc | 780 |
| gacccagccc | agggcaaccc | caatgaggag | gtggcgaggt | tctatgctgc agccatgagt | 840 |

```
ggggctgggc cctgggcagc ctggcctttc ctgcttagcc tggccctaat gctgctgtgg    900
ctgctcagct gacctccttt taccttctga tacctggaaa tccctgccct gttcagcccc    960
acagctccca actatttggt tcctgctcca tggtcgggcc tctgacagcc actttgaata   1020
aaccagacac cg                                                       1032

<210> SEQ ID NO 3
<211> LENGTH: 1104
<212> TYPE: DNA
<213> ORGANISM: H. Sapiens

<400> SEQUENCE: 3
tggaggcctg gctggtgctc acatacaata attaactgct gagtggcctt cgcccaatcc     60
caggctccac tcctgggctc cattcccact ccctgcctgt ctcctaggcc actaaaccac    120
agctgtcccc tggaataagg caaggggag tgtagagcag agcagaagcc tgagccagac     180
ggagagccac ctcctctccc agggacagac atggctcagc ggatgacaac acagctgctg    240
ctccttctag tgtgggtggc tgtagtaggg gaggctcaga caaggattgc atgggccagg    300
actgagcttc tcaatgtctg catgaacgcc aagcaccaca aggaaaagcc aggccccgag    360
gacaagttgc atgagcagtg tcgaccctgg aggaagaatg cctgctgttc taccaacacc    420
agccaggaag cccataagga tgtttcctac ctatatagat tcaactggaa ccactgtgga    480
gagatggcac ctgcctgcaa acggcatttc atccaggaca cctgcctcta cgagtgctcc    540
cccaacttgg ggccctggat ccagcaggtg atcagagctg gcgcaaaga gcgggtactg     600 aacgtgcccc tgtgcaaaga ggactgtgag caatggtggg aagattgtcg cacctcctac    660
acctgcaaga gcaactggca aagggctgg aactggactt cagggtttaa caagtgcgca    720
gtgggagctg cctgccaacc tttccatttc tacttcccca cacccactgt tctgtgcaat    780
gaaatctgga ctcactccta caggtcagc aactacagcc gagggagtgg ccgctgcatc    840
cagatgtggt tcgacccagc ccagggcaac cccaatgagg aggtggcgag gttctatgct    900
gcagccatga gtggggctgg gccctgggca gcctggcctt tcctgcttag cctggcccta    960
atgctgctgt ggctgctcag ctgacctcct tttaccttct gatacctgga aatccctgcc   1020
ctgttcagcc ccacagctcc caactatttg gttcctgctc catggtcggg cctctgacag   1080
ccactttgaa taaaccagac accg                                         1104

<210> SEQ ID NO 4
<211> LENGTH: 939
<212> TYPE: DNA
<213> ORGANISM: H. Sapiens

<400> SEQUENCE: 4
cattccttgg tgccactgac cacagctctt tcttcaggga cagacatggc tcagcggatg     60
acaacacagc tgctgctcct tctagtgtgg gtggctgtag taggggaggc tcagacaagg    120
attgcatggg ccaggactga gcttctcaat gtctgcatga acgccaagca ccacaaggaa    180
aagccaggcc ccgaggacaa gttgcatgag cagtgtcgac cctggaggaa gaatgcctgc    240
tgttctacca acaccagcca ggaagcccat aaggatgttt cctacctata tagattcaac    300
tggaaccact gtggagagat ggcacctgcc tgcaaacggc atttcatcca ggacacctgc    360
ctctacgagt gctcccccaa cttggggccc tggatccagc aggtggatca gagctggcgc    420
aaagagcggg tactgaacgt gcccctgtgc aaagaggact gtgagcaatg gtgggaagat    480
```

```
tgtcgcacct cctacacctg caagagcaac tggcacaagg gctggaactg gacttcaggg    540
tttaacaagt gcgcagtggg agctgcctgc caaccttttc atttctactt ccccacaccc    600
actgttctgt gcaatgaaat ctggactcac tcctacaagg tcagcaacta cagccgaggg    660
agtggccgct gcatccagat gtggttcgac ccagcccagg caaccccaa tgaggaggtg     720 gcgaggttct atgctgcagc catgagtggg gctgggccct gggcagcctg gcctttcctg    780
cttagcctgg ccctaatgct gctgtggctg ctcagctgac ctcctttta cttctgatac     840 ctggaaatcc ctgccctgtt cagccccaca gctcccaact atttggttcc tgctccatgg    900
tcgggcctct gacagccact ttgaataaac cagacaccg                           939

<210> SEQ ID NO 5
<211> LENGTH: 1331
<212> TYPE: DNA
<213> ORGANISM: H. Sapiens

<400> SEQUENCE: 5
ggaaaggatt ttctcagccc ccatccccag cactgtgtgt tggccgcacc catgagagcc    60
tcagcactct gaaggtgcag ggggcaaagg ccaaaagagc tctggcctga acttgggtgg    120
tccctactgt gtgacttggg gcatggccct catctgtgct gaaatgattc cacaaagatt    180
aaactggcta tcatttgttg atttcccct tcttacattt aatccttgca ggagaaagct     240
aagcctcaag atagtttgct tctctttccc ccaaggccaa ggagaaggtg gagtgagggc    300
tggggtcggg acaggttgaa cgggaaccct gtgctctaaa cagttagggt ttgttcccgc    360
aggaactgaa cccaaaggat cacctggtat tccctgagag tacagatttc tccggcgtgg    420
ccctcaaggg acagacatgg ctcagcggat gacaacacag ctgctgctcc ttctagtgtg    480
ggtggctgta gtaggggagg ctcagacaag gattgcatgg gccaggactg agcttctcaa    540
tgtctgcatg aacgccaagc accacaagga aaagccaggc cccgaggaca gttgcatga    600 gcagtgtcga ccctggagga agaatgcctg ctgttctacc aacaccagcc aggaagccca    660
taaggatgtt tcctacctat atagattcaa ctggaaccac tgtggagaga tggcacctgc    720
ctgcaaacgg catttcatcc aggacacctg cctctacgag tgctccccca acttggggcc    780
ctggatccag caggtggatc agagctggcg caaagagcgg gtactgaacg tgcccctgtg    840
caaagaggac tgtgagcaat ggtgggaaga ttgtcgcacc tcctacacct gcaagagcaa    900
ctggcacaag ggctggaact ggacttcagg gtttaacaag tgcgcagtgg gagctgcctg    960
ccaacctttc catttctact tccccacacc cactgttctg tgcaatgaaa tctggactca    1020
ctcctacaag gtcagcaact acagccgagg gagtggccgc tgcatccaga tgtggttcga    1080
cccagcccag gcaaccccca tgaggaggt ggcgaggttc tatgctgcag ccatgagtgg     1140
ggctgggccc tggcagcct ggcctttcct gcttagcctg gccctaatgc tgctgtggct     1200
gctcagctga cctccttta ccttctgata cctggaaatc ctgccctgt tcagccccac      1260 agctcccaac tatttggttc ctgctccatg gtcgggcctc tgacagccac tttgaataaa    1320
ccagacaccg c                                                         1331

<210> SEQ ID NO 6
<211> LENGTH: 929
<212> TYPE: DNA
<213> ORGANISM: H. Sapiens

<400> SEQUENCE: 6
agggacagac atggctcagc ggatgacaac acagctgctg ctccttctag tgtgggtggc    60
```

```
tgtagtaggg gaggctcaga caaggattgc atgggccagg actgagcttc tcaatgtctg    120
catgaacgcc aagcaccaca aggaaaagcc aggccccgag acaagttgc atgagcagtg     180 tcgaccctgg aggaagaatg cctgctgttc taccaacacc agccaggaag cccataagga    240
tgtttcctac ctatatagat tcaactggaa ccactgtgga gagatggcac ctgcctgcaa    300
acggcatttc atccaggaca cctgcctcta cgagtgctcc cccaacttgg ggccctggat    360
ccagcaggtg gatcagagct ggcgcaaaga gcgggtactg aacgtgcccc tgtgcaaaga    420
ggactgtgag caatggtggg aagattgtcg caccctcctac acctgcaaga gcaactggca    480
caagggctgg aactggactt cagggtttaa caagtgcgca gtgggagctg cctgccaacc    540
tttccatttc tacttcccca cacccactgt tctgtgcaat gaaatctgga ctcactccta    600
caaggtcagc aactacagcc gagggagtgg ccgctgcatc cagatgtggt tcgacccagc    660
ccagggcaac cccaatgagg aggtggcgag gttctatgct gcagccatga gtggggctgg    720
gccctgggca gcctggcctt tcctgcttag cctggcccta atgctgctgt ggctgctcag    780
ctgacctcct tttaccttct gatacctgga aatccctgcc ctgttcagcc ccacagctcc    840
caactatttg gttcctgctc catggtcggg cctctgacag ccactttgaa taaaccagac    900
accgcacatg tgtcttgaga attatttgg                                     929

<210> SEQ ID NO 7
<211> LENGTH: 10001
<212> TYPE: DNA
<213> ORGANISM: H. Sapiens

<400> SEQUENCE: 7
cttgaatctg ggaggcggag gttgcagtga gccaagatcg tgccactgca ctccagcttg     60
ggctacagag caagtctccg actcaaaaat aaataaataa atgaaaaaat aaaaaaatta    120
atgttaaatc tcaaccccaa agtgaacaca agatgtatgt aacatgtatg tttgcttagt    180
atacatgcat gtggctccct ttcatgaaca ttcatagctt ttcctataac ccattaatat    240
gtatgctagc caacccattt tacataaaac tcctgtccca ccttcctcc ctcaaattgc     300 ctgcttttgg tctcagccaa aggctccact taccagcctg caggttacaa cctgacataa    360
gaaaaaatat tgtttccaaa tatatagatc tggtgatttt aagttgacac ttctcaggtt    420
gtcacaagat tcaggtatgg ctcactgttg caggacataa gctgggatct cctgggaatt    480
ggtctgcttg caggccctag agagccttcc ttcttggttg attttcctct agagatccaa    540
ctgtcttctc aggctcccct gcctgcctcc tccttgggtc ctttcttgtg gcattgccca    600
gattactggg ccccccatttt ccctacactt actgccactc atagtctgat ggttcccaca    660
tctgcatcca acctggactc ttcccctgag ctttcccctc tacaaccacc ttccccgggc    720
caagggcaca caggcacctc gacaaaaacag tgttctatgt ttcttcctgc ccaaacctgc    780
ccctccctct ccctttttccc atctgtggta ccaccatggg ctcagagaat aaaaaaaatg    840
aaggcttctg tcattgactg gggtggagat ggagggaaga gttagcccag aatcacaggt    900
gctgtagaaa ggatacctga gttgccggga gaggggtcc atgagttggg gatggaagga    960
gagcttggcc cttcaaacaa ttgaagatct gatcaaaaga ttcagaacat ctgtgatttt   1020
gtggctggtg atgggtgaca cctgggctaa tggggttggg ggagttggtg gctctacaat   1080 ttatggccctt gggagatcct tgctctctat agctgactgg gaggttggaa gcctgggctc   1140
tagcccttgc cttgatcctc cggatctcat tttcctcatc tgcctaacag gacagagggg   1200
```

```
ttggaaactg atgagattag ctcaaaggat cctggcagct caggctgcaa gattttttc      1260
agacctcagt gtttgggaaa aaattgggta ggtggagctt agggactggc cttaggcctg     1320
cactgttaat tcaccccctc ccactacccc atggaggcct ggctggtgct cacatacaat     1380
aattaactgc tgagtggcct tcgcccaatc ccaggctcca ctcctgggct ccattcccac     1440
tccctgcctg tctcctaggc cactaaacca cagctgtccc ctggaataag gcaaggggga     1500
gtgtagagca gagcagaagc ctgagccaga cggagagcca cctcctctcc caggtatgtg     1560
acactcccca tcccccttca gaggccacac accctatggc attcccacca tgtgttaagg     1620
atttctgaa ctgaagggc cctctgtttg cctgaaggcc agagaatctt gaagtggaga       1680
ctgaggccca gaccagagtg tggcctgctc aaggttaaac gacaagttag tgttcatccc     1740
cctgaactag tacctgggct ctagcccttc agtccagagc tgagttctca gctcttctag     1800
tctggggccc caaggttggg tgtggggtc atgattgttg gtggggaggg gtcacagctg      1860
gactaagacc tgaaggtgag actaggcagg tgggaaagga gcttgcagag tgatgctgct    1920
caaaaggaca ggaagagagc ctggcttcag aagcagccac agcaagagag actactgact    1980
gaacaggtgg gctccactgg gggctgggga aaggattttc tcagccccca tccccagcac    2040
tgtgtgttgg ccgcacccat gagagcctca gcactctgaa ggtgcagggg gcaaaggcca    2100
aaagagctct ggcctgaact tgggtggtcc tactgtgtg acttggggca tggccctcat     2160
ctgtgctgaa atgattccac aaagattaaa ctggctatca tttgttgatt tcccccttct    2220
tacatttaat ccttgcagga gaaagctaag cctcaagata gtttgcttct ctttccccca    2280
aggccaagga gaaggtggag tgagggctgg ggtcgggaca ggttgaacgg gaaccctgtg    2340
ctctaaacag ttagggtttg ttcccgcagg aactgaaccc aaaggatcac ctggtattcc    2400
ctgagagtac agatttctcc ggcgtggccc tcaaggttag tgagtgagca ggtccacagg    2460
ggcatgattg gatcctggaa tgaatgaatc aaccatgaga gagtgaatga acactggaat    2520
caatagagta gcagagtaat ggattgtgga gcaggaaaga gagctgctgg gtgggaattc    2580
aattccaggc ttatatgagc cctgctgtgc agtcggcctg gagacagccc agctcaggcc    2640
ctgcctagac ccctgtcaag gaggccctgt caagaggaga ggaggggcag cacggggca     2700
aggcaagctt gtgagcggga aaggcatgtc cactttagcg actggtatgt ggaagatgag    2760
ttagaggaga cagatggaga gaagtcatag gaaataaatt ctgagcattt taggagggcc    2820
cagacacctg tgtccagtg gagtgaagga aacagtcgcc tcccaaaatt cagtgtctga    2880
ggtcaaagga ttgaagttct gtgatgacca aggagaagcc agctctgtgg tagggggcac   2940
aggagctccc caaggcccca gggctgtcca gctggctgtc ccctgccagc acccatgtcc    3000
tgtgacccca ccccaccaag atcccatggt ttccgggaag ggcctactaa actagcttga   3060
gtgatgaggc tagaaagggg ctgggaccaa ggtttaaaaa gcaaaacaaa ctaacaaaaa    3120
ccacactgca gccccccaa ctaaaacatt tttataaact tttttttttt ttttgagatg    3180
gagtctcgct ctgtcaccca ggctagagtg caatggcaca atcttggctc actgtaacct    3240
ccacctcctg gattcaagtg attctcctgc ctcagcctcc cacgtagctg ggactacagg    3300
cacacgacac cgcacccagc tcatttgta tttttagtag acacagggtt tcactatgtt     3360
ggccaggctg gtctcaaact tctgacctca ggtgatccac ccacctcagc cttccaaagt    3420
gctgggatta caggcatgag ccaccgcgcc cagcccattt ttgtaaactt ttacaatgaa    3480
gtaatttggt gtcaaaatct gacctgaaaa ttaatgtgag tttatgtata gttttaattt    3540
atcccactag tgtaactgtt tcaccccaga atatacactt gattattggg tatatgaaaa    3600
```

```
ttatattttc tttgaatcac ctttgatgaa atcctaaaaa attttaaccc tgaaacattt    3660
gaataaggca ttgtggacct atggcaaact cctggctatt tctgcatttt gcccaaatcc    3720
atccttgaat tatatcacct gaacctcgtg accacctgga gaaggcaatg aggctcaagc    3780
cagggagggg tggtgtctaa tcctaccttt cattggatct gggaaaactg agggagatgg    3840
gggcagggct ctatctgccc caggcttccg tccaggcccc accctcctgg agccctgcac    3900
acaacttaag gccccacctc cgcattcctt ggtgccactg accacagctc tttcttcagg    3960
gacagacatg gctcagcgga tgacaacaca gctgctgctc cttctagtgt gggtggctgt    4020
agtaggggag gctcagacaa ggattgcatg ggccaggact gagcttctca atgtctgcat    4080
gaacgccaag caccacaagg aaaagccagg ccccgaggac aagttgcatg agcaggtggg    4140
ccagggggtg atctggggtg gtgagggact ggctcaggaa gaggaaacga ggacatggaa    4200
atgccaaacc ccattcactg gtgaactgaa gtggaggagc cttcagtttt gcattaatat    4260
gggtgactat ttcacagaca ctgtgccaaa tgtcggtaca atgccaacag ttcaccttct    4320
tggttgttga gtttccgcat tacagaaata aggaagcagg cccaaggag agcctgggaa    4380
atgaagttgg agtgacccat cctggggttg cttgatttag ggatttagac tgggaatgac    4440
tcctccaaag atctgaggga agaaactgca cactgtgcat agtggcctct tttctgccag    4500
ccctaaacag ctcaagaagg gagagtctct cacattatga ggctgtgtgc aaagcattct    4560
ttttttttt tcctgagaca aagtctccat atgttgccca ggctggtctc aaattcctgg    4620
actcaagtga tcctcccacc tcagcctccc aaagtgtggg attacagaaa tgagccgtac    4680
gccctcctga agcatcttgg ttcatgcatc tcgcaaaact tgggctgtg tctctcgacc    4740
acattggacc tgaggtctcc ctataacatt tattttgcta ccacccttt aatatcctga    4800
acatgatgat ataactaaag aaaaagcaga ggaaaagtaa tttgtaggcc aggtgttacg    4860
gctcacgcct gtaatcccaa cactgtggga tgtcgagatg ggcagatcac ttgagctcag    4920
gagttcgaga ccagcctggg caagatggca aaaccccatc tctactaaaa aataaaaaaa    4980
attagtcagg tgtggtggca catgcctgca gtcccagcta ctcaggaggc tgaggtgggc    5040
aggtcagttg agcccaggag gcagagattg tagatcgtgc cactgcactc cagcctgggc    5100
aacagagtga gaccttgtca aagaaagaa agaacgaaaa aaagaaagaa aggaaggaag    5160
gaagggagg aaggaaaggg agggaggaaa gggagggagg aaagggaggg aggcaaggga    5220
gagaaacttg taatacgcat ttctttttt ttttcttgag atagagtttt gctcttgttg    5280
cccagggtgg agtgcagtgg cacaatctca gctcactgca acctccacct cccaggttca    5340
agtgattctc ctgcctcagc ctcctgagta ggcacacgcc accacaccca gctaatttt    5400
tgtttgtttg tttgttttgt tgttggtat ttttagtaga gatgggggtt tcaccatgtt    5460
ggccaggctg gtctcgaact cctcacctca taatccgccc ctcttggcct cccaaagtgc    5520
tgagattaca ggtgtgagcc actgcgcccg gccttaagtg cacattttat ttatttattt    5580
atttatttat ttattgagat ggagtcttgc tctgttgccc aggctggagt gcagtggcac    5640
aatctcagct cactgcaacc tccacctccc aggttcaagc aattctcctg ccttggcctc    5700
cagagtagct gggactatag gcacctgcca ccatgcctag ctaattttg tattttagt    5760
agaaatgggg ttttgccatg ttggccaggc tggtctccat tcttgacctt aagtgatctg    5820
tccacctcca cctcccaaag tgctgggatt acaggcacta tgtgagccac gtgccggcc    5880
cacattttaa tatttagctt gtcagcctta agtaatgaga ttcaggaagc ttgaggatag    5940
```

```
gcacacagga gcatagtttc aagttgtcct gaattttgca gccatcacaa gttagttttt      6000
aaggaaaaag attagttcct aagttgtttc tcaataactt ataataaaat aacatccaca      6060
attgattggc tatacattgt ttttttgtat cacaaattcc acaaacagat aatgggtgag      6120
gcagctagtc agggacaaaa cacttcccaa gtagctggga ttacaggtgt ccgccaccac      6180
acttggctag ttttttgttt gtttattttt tgagatggag tcttgctctg tcgcccaggc      6240
tggagtgcag tggcatgatc tcggctcact gcaagctcca cctgccgggt tcacaccatt      6300
ctcctgcctc agcctcccaa gtagctggga ctacaggtgc cagccaccac gcccggctaa      6360
ttttttgtat ttttagtaga cgggggttt caccatgttg ccaggatgg tcttgatctc       6420 ttagcctcgt gatccacccg cctcggcctc ccaaaatgct gggattacag gcgtgagcca      6480
ccgcacccgg cctaattttt atattttag tagagacggg gtttcaccat gttgccagg        6540 ctggtctcaa actcttgatc tcaggtgatc cacctgcctt ggcctcccaa agtgctggga      6600
ttacacaagt aagccactgc acccagcctg gggttacaat ttaaattgct tttttacctt      6660
caaatctttg acacctcagt gaggcttaat ctgaccgcac tattacacta caagtcccca      6720
tccgtctctg cttaatttt gtccaaagca aaaatcaggt gatgtgttca ttgttgtaac       6780
cccagtttct acaaaagtac ctgggtgaga gtaagtagga tctcaataaa ggttgaatta     6840
acaaattttg taatgactgc aactccagca ggagctccct tttgggctcc cactgtctct     6900
gacggccctc tcccctaaag aggtcccaat agcaagtatt ttcctgggtg acttccagtg     6960
ggctggggaa tcaaggacta agaggggaga cactgcatgt ggaatattct ggctgtgctg     7020
gctgtgctgg ctgtggactg agtcctctgt cttcccccat ccagtgtcga ccctggagga     7080
agaatgcctg ctgttctacc aacaccagcc aggaagccca taaggatgtt tcctacctat     7140
atagattcaa ctggaaccac tgtggagaga tggcacctgc ctgcaaacgg catttcatcc     7200
aggacacctg cctctacgag tgctccccca acttggggcc ctggatccag caggtatgca     7260
tggcttcctg caggtacaag acctagcgga gcagctgagc tttccaggca tctctgcagg     7320
ctgcaacccc agctccagtt ctattcgggg ctgagttgct gggattcttg aacctgagcc     7380
cttcttttgt atcaaaatca cccaggtgga tcagagctgg cgcaaagagc gggtactgaa     7440
cgtgcccctg tgcaaagagg actgtgagca atggtgggaa gattgtcgca cctcctacac     7500
ctgcaagagc aactggcaca agggctggaa ctggacttca ggtgagggct ggggtgggca    7560
ggaatggagg gatttggaag tggaggtgtg tgggtgtgga acaggtatgt gacaatttgg     7620
agttgtaggg ctggcagacc tcaagatagt tccgggccca gtggctaaag gtcttccctc     7680
ctctctacag ggtttaacaa gtgcgcagtg ggagctgcct gccaacctt ccatttctac      7740 ttccccacac ccactgttct gtgcaatgaa atctggactc actcctacaa ggtcagcaac     7800
tacagccgag ggagtggccg ctgcatccag atgtggttcg acccagccca gggcaacccc    7860
aatgaggagg tggcgaggtt ctatgctgca gccatgagtg gggctgggcc ctgggcagcc    7920
tggcctttcc tgcttagcct ggccctaatg ctgctgtggc tgctcagctg acctcctttt     7980
accttctgat acctggaaat ccctgccctg ttcagcccca cagctcccaa ctatttggtt     8040
cctgctccat ggtcgggcct ctgacagcca ctttgaataa accagacacc gcacatgtgt    8100
cttgagaatt atttggatat gaatgggaac gtgactgttt tgttttccaa ttcccattga     8160
ttgaaaccag tgagactggg ccaattccta gctctgacag ttgctataaa ctagcctgat    8220
acttaactat ttttctaact taggagacat tcgtagctct caatttcatt ttttactatt    8280
gctccaatct agagccaagc ccaggaattt ttcatttgtt tgttttgaga cagggtctca    8340
```

-continued

```
cccaggaata ttttgtttgt tttgagacag gatctcactc tgtcaccagg ctggagtgca    8400
gtggcatgac cttgattcac tgtaacatct gcctcctggg ctcaagtgat cctcccacct    8460
cagcctctca acttgagact gcaaccatgt gccaccacac ctggctaatt ttttttcttt    8520
ttttgagatg gagtttcgct cttgttgccc aggctggagt gcaatggcat gatcttggcc    8580
cactgcaacc tcctcctccc aagttcaagt gattctcttg cctcagcctc cagagtagct    8640
gggattatag gcatgcacca ccatgcccgg ctgattttgt atttttagta gagacagggt    8700
ttctccatgt tggtcaggct ggtcttgaac tcccgacctc aagtgatccg cctgccttgg    8760
cctcccaaag tgctgggatt acaggcgtga gccactgcgc ccagcccac ctggctaatt    8820
gttacatttt tttataaaga ggagatcttg gtatgtcgtc caggctgatc tcaaactcct    8880
ggcctgaagc aaacctttca tctcagactt caaaagtact gggattacaa ccgtgagcca    8940
ccacacccag cgcagtctca gctcactgca acctctgcct cccacattca agcaattctg    9000
cctcagcctc ccgagtacct gggactatag gtgtgggcca ccatgcctgg ctaattttg    9060
tatttttatt agagatgggg tttcgccatg ttggccaagc tggtctggaa ctcctaacct    9120
caggtgaacc acccacctca gcctcccaaa gtgctgggat tacaagtgtg agacaccatg    9180
cccagcctag ctcaggattt tatcatttaa actgaacata agcttcccag ggttgattcc    9240
tgtgctgtgc tcagctctcc aaaagaagag gtgggaatgg ctgtacccag catgttttgg    9300
atgggttgct gggaagaggg taagggtggc agcaagagcc atatggcact aacagctaat    9360
acccacaaag cattttctgc taggcactat cctaaactgt ttataccgat gacatgtaga    9420
tactactgtc tgcatttttcc atatgtagaa acagacacat aaattaaaga acattgcctg    9480
gccaggcaca gtggctcaca cctataatcc cagctctttg ggaggccaag tcgggcggat    9540
cacctgaggt caggagttcg agattagcct agccaacatg gcaaaaccct gtctctacta    9600
aaaatacaaa acttagccgg acgtggtggt gtgcacctgt aatcccagct actcgggagg    9660
ctgaggcagg agaatctctc gaacccagga ggcagaagtt gcagtgacca gagatcacac    9720
cattgcactc ctgcctgggc aacagagcga aactccgcct caaaaaaaaa aaaaaaaaa    9780
aaagaaagga catgctcttt cccatcatgg agtgaataaa tatgtgtgtc ttgaagggat    9840
aatgggtcca tggctgacca gaggagctgg gcctaagctg ctctgccaga gctaggatgg    9900
gaacccaaac ttcgactcct aagcaggttc caaaccaata acctgaaggg ttttaaggca    9960
gcgttctcca ttaaatatag tttgtaacct ttgtattaag c                       10001
```

<210> SEQ ID NO 8
<211> LENGTH: 20
<212> TYPE: DNA
<213> ORGANISM: Artificial Sequence
<220> FEATURE:
<223> OTHER INFORMATION: Forward primer

<400> SEQUENCE: 8
gaaatccctg ccctgttcag                                                20

<210> SEQ ID NO 9
<211> LENGTH: 17
<212> TYPE: DNA
<213> ORGANISM: Artificial Sequence
<220> FEATURE:
<223> OTHER INFORMATION: Reverse primer

<400> SEQUENCE: 9

-continued agaggcccga ccatgga                                            17

<210> SEQ ID NO 10
<211> LENGTH: 16
<212> TYPE: DNA
<213> ORGANISM: Artificial Sequence
<220> FEATURE:
<223> OTHER INFORMATION: Probe

<400> SEQUENCE: 10
agctcccaac tatttg                                             16

<210> SEQ ID NO 11
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 11
attctcaaga cacatgtgcg                                         20

<210> SEQ ID NO 12
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 12
cagttcctgg gagaggaggt                                         20

<210> SEQ ID NO 13
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 13
caggtgatcc tttgggttca                                         20

<210> SEQ ID NO 14
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 14
gaataccagg tgatcctttg                                         20

<210> SEQ ID NO 15
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 15
tcagggaata ccaggtgatc                                         20

<210> SEQ ID NO 16
<211> LENGTH: 20
<212> TYPE: DNA
<213> ORGANISM: Artificial Sequence

```
<220> FEATURE:
<223> OTHER INFORMATION: Synthetic Antisense Oligonucleotide

<400> SEQUENCE: 16
tactctcagg gaataccagg                                              20

<210> SEQ ID NO 17
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 17
gggccacgcc ggagaaatct                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 18
tgttgtcatc cgctgagcca                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 19
cacactagaa ggagcagcag                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 20
tactacagcc acccacacta                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 21
catgcaatcc ttgtctgagc                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 22
cagtcctggc ccatgcaatc                                              20
```

<210> SEQ ID NO 23
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 23
gtcgacactg ctcatgcaac                                         20

<210> SEQ ID NO 24
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 24
tccagggtcg acactgctca                                         20

<210> SEQ ID NO 25
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 25
tatataggta ggaaacatcc                                         20

<210> SEQ ID NO 26
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 26
atctatatag gtaggaaaca                                         20

<210> SEQ ID NO 27
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 27
gctcttgcag gtgtaggagg                                         20

<210> SEQ ID NO 28
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 28
ccactgcgca cttgttaaac                                         20

<210> SEQ ID NO 29
<211> LENGTH: 20
<212> TYPE: DNA
<213> ORGANISM: Artificial Sequence
<220> FEATURE:
<223> OTHER INFORMATION: Synthetic Antisense Oligonucleotide

```
<400> SEQUENCE: 29
aggaggtcag ctgagcagcc                                          20

<210> SEQ ID NO 30
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 30
aggtaaaagg aggtcagctg                                          20

<210> SEQ ID NO 31
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 31
atcagaaggt aaaaggaggt                                          20

<210> SEQ ID NO 32
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 32
ggcagggatt tccaggtatc                                          20

<210> SEQ ID NO 33
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 33
ggaaccaaat agttgggagc                                          20

<210> SEQ ID NO 34
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 34
catggagcag gaaccaaata                                          20

<210> SEQ ID NO 35
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 35
tcagaggccc gaccatggag                                          20

<210> SEQ ID NO 36
```

```
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 36
tggtttattc aaagtggctg                                              20

<210> SEQ ID NO 37
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 37
gtgtctggtt tattcaaagt                                              20

<210> SEQ ID NO 38
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 38
tgtatgtgag caccagccag                                              20

<210> SEQ ID NO 39
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 39
gattgggcga aggccactca                                              20

<210> SEQ ID NO 40
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 40
cctaggagac aggcagggag                                              20

<210> SEQ ID NO 41
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 41
ccccttgcct tattccaggg                                              20

<210> SEQ ID NO 42
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 42
```

```
tggtcagtgg caccaaggaa                                              20

<210> SEQ ID NO 43
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 43
tgtccctgaa gaaagagctg                                              20

<210> SEQ ID NO 44
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 44
gggctgagaa aatcctttcc                                              20

<210> SEQ ID NO 45
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 45
gcggccaaca cacagtgctg                                              20

<210> SEQ ID NO 46
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 46
gaggctctca tgggtgcggc                                              20

<210> SEQ ID NO 47
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 47
caccttcaga gtgctgaggc                                              20

<210> SEQ ID NO 48
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 48
caggccagag ctcttttggc                                              20

<210> SEQ ID NO 49
<211> LENGTH: 20
<212> TYPE: DNA
```

```
<213> ORGANISM: Artificial Sequence
<220> FEATURE:
<223> OTHER INFORMATION: Synthetic Antisense Oligonucleotide

<400> SEQUENCE: 49
gggaccaccc aagttcaggc                                          20

<210> SEQ ID NO 50
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 50
cagtagggac cacccaagtt                                          20

<210> SEQ ID NO 51
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 51
atgccccaag tcacacagta                                          20

<210> SEQ ID NO 52
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 52
gcacagatga gggccatgcc                                          20

<210> SEQ ID NO 53
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 53
atttcagcac agatgagggc                                          20

<210> SEQ ID NO 54
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 54
tttgtggaat catttcagca                                          20

<210> SEQ ID NO 55
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 55
ccagtttaat ctttgtggaa                                          20
```

<210> SEQ ID NO 56
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 56
aacaaatgat agccagttta                                        20

<210> SEQ ID NO 57
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 57
tgcaaggatt aaatgtaaga                                        20

<210> SEQ ID NO 58
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 58
agagaagcaa actatcttga                                        20

<210> SEQ ID NO 59
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 59
agcacagggt tcccgttcaa                                        20

<210> SEQ ID NO 60
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 60
tgtttagagc acagggttcc                                        20

<210> SEQ ID NO 61
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 61
tcagttcctg cgggaacaaa                                        20

<210> SEQ ID NO 62
<211> LENGTH: 20
<212> TYPE: DNA
<213> ORGANISM: Artificial Sequence
<220> FEATURE:

```
<223> OTHER INFORMATION: Synthetic Antisense Oligonucleotide

<400> SEQUENCE: 62
gagtgtcaca tacctgggag                                                 20

<210> SEQ ID NO 63
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 63
ttcaggcaaa cagagggccc                                                 20

<210> SEQ ID NO 64
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 64
ggatgaacac taacttgtcg                                                 20

<210> SEQ ID NO 65
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 65
cactaacctt gagggccacg                                                 20

<210> SEQ ID NO 66
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 66
tgattccagt gttcattcac                                                 20

<210> SEQ ID NO 67
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 67
gacaccaggt gtctgggccc                                                 20

<210> SEQ ID NO 68
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 68
attaattttc aggtcagatt                                                 20
```

<210> SEQ ID NO 69
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 69
acagttacac tagtgggata                                              20

<210> SEQ ID NO 70
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 70
tacccaataa tcaagtgtat                                              20

<210> SEQ ID NO 71
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 71
ttttaggatt tcatcaaagg                                              20

<210> SEQ ID NO 72
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 72
taggtccaca atgccttatt                                              20

<210> SEQ ID NO 73
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 73
agtttgccat aggtccacaa                                              20

<210> SEQ ID NO 74
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 74
gatttgggca aaatgcagaa                                              20

<210> SEQ ID NO 75
<211> LENGTH: 20
<212> TYPE: DNA
<213> ORGANISM: Artificial Sequence
<220> FEATURE:
<223> OTHER INFORMATION: Synthetic Antisense Oligonucleotide

```
<400> SEQUENCE: 75
tgatataatt caaggatgga                                               20

<210> SEQ ID NO 76
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 76
aatgaaaggt aggattagac                                               20

<210> SEQ ID NO 77
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 77
tcagttcacc agtgaatggg                                               20

<210> SEQ ID NO 78
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 78
tttggaggag tcattcccag                                               20

<210> SEQ ID NO 79
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 79
acctcaggtc caatgtggtc                                               20

<210> SEQ ID NO 80
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 80
gcaaaataaa tgttataggg                                               20

<210> SEQ ID NO 81
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 81
agttatatca tcatgttcag                                               20

<210> SEQ ID NO 82
<211> LENGTH: 20
```

```
<212> TYPE: DNA
<213> ORGANISM: Artificial Sequence
<220> FEATURE:
<223> OTHER INFORMATION: Synthetic Antisense Oligonucleotide

<400> SEQUENCE: 82
ccaatcaatt gtggatgtta                                              20

<210> SEQ ID NO 83
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 83
gcaatttaaa ttgtaacccc                                              20

<210> SEQ ID NO 84
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 84
tacaaaattt gttaattcaa                                              20

<210> SEQ ID NO 85
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 85
tgcaggaagc catgcatacc                                              20

<210> SEQ ID NO 86
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 86
tcaggttcaa gaatcccagc                                              20

<210> SEQ ID NO 87
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 87
aaagaagggc tcaggttcaa                                              20

<210> SEQ ID NO 88
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 88
```

-continued

```
cacctgggtg attttgatac                                              20

<210> SEQ ID NO 89
<211> LENGTH: 19
<212> TYPE: RNA
<213> ORGANISM: Artificial Sequence
<220> FEATURE:
<223> OTHER INFORMATION: Synthetic Antisense Oligonucleotide

<400> SEQUENCE: 89
cgagaggcgg acgggaccg                                               19

<210> SEQ ID NO 90
<211> LENGTH: 21
<212> TYPE: DNA
<213> ORGANISM: Artificial Sequence
<220> FEATURE:
<221> NAME/KEY: misc_feature
<222> LOCATION: 1-19
<223> OTHER INFORMATION: bases at these positions are RNA
<220> FEATURE:
<223> OTHER INFORMATION: Synthetic Antisense Oligonucleotide

<400> SEQUENCE: 90
cgagaggcgg acgggaccgt t                                            21

<210> SEQ ID NO 91
<211> LENGTH: 21
<212> TYPE: DNA
<213> ORGANISM: Artificial Sequence
<220> FEATURE:
<221> NAME/KEY: misc_feature
<222> LOCATION: 3-21
<223> OTHER INFORMATION: bases at these positions are RNA
<220> FEATURE:
<223> OTHER INFORMATION: Synthetic Antisense Oligonucleotide

<400> SEQUENCE: 91
ttgcucuccg ccugcccugg c                                            21

<210> SEQ ID NO 92
<211> LENGTH: 19
<212> TYPE: RNA
<213> ORGANISM: Artificial Sequence
<220> FEATURE:
<223> OTHER INFORMATION: Synthetic Antisense Oligonucleotide

<400> SEQUENCE: 92
gcucuccgcc ugcccuggc                                               19

<210> SEQ ID NO 93
<211> LENGTH: 21
<212> TYPE: DNA
<213> ORGANISM: Artificial Sequence
<220> FEATURE:
<223> OTHER INFORMATION: Synthetic Antisense Oligonucleotide

<400> SEQUENCE: 93
tgttgtcatc cgctgagcca t                                            21

<210> SEQ ID NO 94
<211> LENGTH: 21
<212> TYPE: DNA
<213> ORGANISM: Artificial Sequence
<220> FEATURE:
<223> OTHER INFORMATION: Synthetic Antisense Oligonucleotide

<400> SEQUENCE: 94
```
aggaggtcag ctgagcagcc a                                              21

<210> SEQ ID NO 95
<211> LENGTH: 21
<212> TYPE: DNA
<213> ORGANISM: Artificial Sequence
<220> FEATURE:
<223> OTHER INFORMATION: Synthetic Antisense Oligonucleotide

<400> SEQUENCE: 95
cttgtggtgc ttggcgttca t                                              21

<210> SEQ ID NO 96
<211> LENGTH: 21
<212> TYPE: DNA
<213> ORGANISM: Artificial Sequence
<220> FEATURE:
<223> OTHER INFORMATION: Synthetic Antisense Oligonucleotide

<400> SEQUENCE: 96
gtaggaaaca tccttatggg c                                              21

<210> SEQ ID NO 97
<211> LENGTH: 21
<212> TYPE: DNA
<213> ORGANISM: Artificial Sequence
<220> FEATURE:
<223> OTHER INFORMATION: Synthetic Antisense Oligonucleotide

<400> SEQUENCE: 97
gatccagggc cccaagttgg g                                              21

<210> SEQ ID NO 98
<211> LENGTH: 21
<212> TYPE: DNA
<213> ORGANISM: Artificial Sequence
<220> FEATURE:
<223> OTHER INFORMATION: Synthetic Antisense Oligonucleotide

<400> SEQUENCE: 98
gctcttgcag gtgtaggagg t                                              21

<210> SEQ ID NO 99
<211> LENGTH: 21
<212> TYPE: DNA
<213> ORGANISM: Artificial Sequence
<220> FEATURE:
<223> OTHER INFORMATION: Synthetic Antisense Oligonucleotide

<400> SEQUENCE: 99
ttcattgcac agaacagtgg g                                              21

<210> SEQ ID NO 100
<211> LENGTH: 21
<212> TYPE: DNA
<213> ORGANISM: Artificial Sequence
<220> FEATURE:
<223> OTHER INFORMATION: Synthetic Antisense Oligonucleotide

<400> SEQUENCE: 100
cgccacctcc tcattggggt t                                              21

<210> SEQ ID NO 101
<211> LENGTH: 19
<212> TYPE: DNA

```
<213> ORGANISM: Artificial Sequence
<220> FEATURE:
<223> OTHER INFORMATION: Synthetic Antisense Oligonucleotide

<400> SEQUENCE: 101
cttggcgttc atgcagaca                                                    19

<210> SEQ ID NO 102
<211> LENGTH: 19
<212> TYPE: DNA
<213> ORGANISM: Artificial Sequence
<220> FEATURE:
<223> OTHER INFORMATION: Synthetic Antisense Oligonucleotide

<400> SEQUENCE: 102
atataggtag gaaacatcc                                                    19

<210> SEQ ID NO 103
<211> LENGTH: 19
<212> TYPE: DNA
<213> ORGANISM: Artificial Sequence
<220> FEATURE:
<223> OTHER INFORMATION: Synthetic Antisense Oligonucleotide

<400> SEQUENCE: 103
ccattgctca cagtcctct                                                    19

<210> SEQ ID NO 104
<211> LENGTH: 19
<212> TYPE: DNA
<213> ORGANISM: Artificial Sequence
<220> FEATURE:
<223> OTHER INFORMATION: Synthetic Antisense Oligonucleotide

<400> SEQUENCE: 104
ggagtgagtc cagcccact                                                    19
```

MODULATION OF FR-ALPHA EXPRESSION

CROSS-REFERENCE TO RELATED APPLICATIONS

This application claims priority to U.S. provisional application Ser. No. 60/884,121 filed on Jan. 9, 2007, entitled "MODULATION OF FR-ALPHA EXPRESSION", which is herein incorporated by reference in its entirety.

INCORPORATION OF SEQUENCE LISTING

The present application is being filed along with a Sequence Listing in electronic format. The Sequence Listing is provided as a file entitled BIOL0076USSEQ.txt, created Jan. 8, 2008, which is 38.4 Kb in size. The information in the electronic format of the sequence listing is incorporated herein by reference in its entirety.

BACKGROUND

Folate is essential for normal cell growth and replication and is required for biochemical processes such as DNA and RNA synthesis and transmethylation reactions. The human alpha isoform folate receptor (FR-alpha; also known as folate receptor 1 (adult); FBP; FOLR; FOLR1; and MOv18) has a very high affinity for folic acid and is an essential component for cellular accumulation of folates and folate analogs used in the treatment of cancer.

Lacey et al. isolated a nearly full-length cDNA from a human carcinoma cell line library, and Elwood isolated human cDNA clones from human malignant nasopharyngeal carcinoma cell and placental cDNA libraries (Elwood, J Biol Chem, 1989, 264, 14893-14901; Lacey et al., J Clin Invest, 1989, 84, 715-720). Human FR-alpha levels have been found to be elevated in many cancer cell types. For example, the FR-alpha is highly overexpressed in some solid epithelial tumors such as ovarian carcinoma and mesothelioma. Other cancers with elevated levels include breast, brain, and colorectal cancers. FR-alpha has also been found to be a cofactor for cellular entry for Marburg and Ebola viruses (Chan et al., Cell, 2001, 106, 117-126).

Antisense technology is an effective means for reducing the expression of one or more specific gene products and is uniquely useful in a number of therapeutic, diagnostic, and research applications.

Disclosed herein are antisense compounds useful for modulating expression of FR-alpha via antisense mechanisms of action such as RNaseH, RNAi and dsRNA enzymes, as well as other antisense mechanisms based on target degradation or target occupancy. One having skill in the art, once armed with this disclosure will be able, without undue experimentation, to identify, prepare and exploit antisense compounds for these uses.

SUMMARY

Provided herein are oligomeric compounds, especially nucleic acid and nucleic acid-like oligomers, which are targeted to a nucleic acid encoding FR-alpha. Further provided are antisense compounds which are oligomeric compounds that modulate the expression of FR-alpha. Also contemplated is a method of making an oligomeric compound comprising specifically hybridizing in vitro a first oligomeric strand comprising a sequence of at least 8 contiguous nucleobases of any of the sequences set forth in Table 6 to a second oligomeric strand comprising a sequence substantially complementary to said first strand.

Further provided are methods of modulating the expression of FR-alpha in cells, tissues or animals comprising contacting said cells, tissues or animals with one or more of the compounds or compositions provided herein. For example, in one embodiment, the compounds or compositions can be used to inhibit the expression of FR-alpha in cells, tissues or animals.

Further provided are methods of identifying the relationship between FR-alpha and a disease state, phenotype, or condition by detecting or modulating FR-alpha comprising contacting a sample, tissue, cell, or organism with one or more oligomeric compounds, measuring the nucleic acid or protein level of FR-alpha and/or a related phenotypic or chemical endpoint coincident with or at some time after treatment, and optionally comparing the measured value to a non-treated sample or sample treated with a further compound, wherein a change in said nucleic acid or protein level of FR-alpha coincident with said related phenotypic or chemical endpoint indicates the existence or presence of a predisposition to a disease state, phenotype, or condition.

Further provided are methods of screening for modulators of expression of FR-alpha by contacting a target segment of a nucleic acid molecule encoding FR-alpha with one or more candidate modulators, and selecting for one or more candidate modulators which decrease or increase the expression of a nucleic acid molecule encoding FR-alpha.

Further provided are methods of screening for additional modulators of expression of FR-alpha by contacting a validated target segment of a nucleic acid molecule encoding FR-alpha with one or more candidate modulators, and selecting for one or more candidate modulators which decrease or increase the expression of a nucleic acid molecule encoding FR-alpha.

Pharmaceutical, therapeutic and other compositions comprising the compounds described herein are also provided.

Also provided is the use of the compounds or compositions in the manufacture of a medicament for the treatment of one or more conditions associated with a target nucleic acid. Further contemplated are methods where cells or tissues are contacted in vivo with an effective amount of one or more of the compounds or compositions provided herein. Also provided are ex vivo methods of treatment that include contacting cells or tissues with an effective amount of one or more of the compounds or compositions and then introducing said cells or tissues into an animal.

DETAILED DESCRIPTION

Overview

Disclosed herein are oligomeric compounds, including antisense oligonucleotides and other antisense compounds for use in modulating the expression of nucleic acid molecules encoding FR-alpha. This is accomplished by providing oligomeric compounds which hybridize with one or more target nucleic acid molecules encoding FR-alpha. As used herein, the terms "target nucleic acid" and "nucleic acid molecule encoding FR-alpha" have been used for convenience to encompass DNA encoding FR-alpha, RNA (including pre-mRNA and mRNA or portions thereof) transcribed from such DNA, and also cDNA derived from such RNA.

The principle behind antisense technology is that an antisense compound, which hybridizes to a target nucleic acid, modulates gene expression activities such as transcription or translation. This sequence specificity makes antisense compounds extremely attractive as tools for target validation and gene functionalization, as well as therapeutics to selectively modulate the expression of genes involved in disease.

Antisense Mechanisms

Antisense mechanisms are all those involving the hybridization of a compound with target nucleic acid, wherein the outcome or effect of the hybridization is either target degradation or target occupancy with concomitant stalling of the cellular machinery involving, for example, transcription or splicing.

Target degradation can include an RNase H. RNase H is a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of DNA-like oligonucleotide-mediated inhibition of gene expression.

Target degradation can include RNA interference (RNAi). RNAi is a form of posttranscriptional gene silencing that was initially defined in the nematode, Caenorhabditis elegans, resulting from exposure to double-stranded RNA (dsRNA). In many species the introduction of double-stranded structures, such as double-stranded RNA (dsRNA) molecules, has been shown to induce potent and specific antisense-mediated reduction of the function of a gene or its associated gene products. The RNAi compounds are often referred to as short interfering RNAs or siRNAs. Recently, it has been shown that it is, in fact, the single-stranded RNA oligomers of antisense polarity of the siRNAs which are the potent inducers of RNAi (Tijsterman et al., Science, 2002, 295, 694-697).

Both RNAi compounds (i.e., single- or double-stranded RNA or RNA-like compounds) and single-stranded RNase H-dependent antisense compounds bind to their RNA target by base pairing (i.e., hybridization) and induce site-specific cleavage of the target RNA by specific RNAses; i.e., both are antisense mechanisms (Vickers et al., 2003, J. Biol. Chem., 278, 7108-7118). Double-stranded ribonucleases (dsRNases) such as those in the RNase III and ribonuclease L family of enzymes also play a role in RNA target degradation. Double-stranded ribonucleases and oligomeric compounds that trigger them are further described in U.S. Pat. Nos. 5,898,031 and 6,107,094.

Nonlimiting examples of an occupancy-based antisense mechanism whereby antisense compounds hybridize yet do not elicit cleavage of the target include inhibition of translation, modulation of splicing, modulation of poly(A) site selection and disruption of regulatory RNA structure. A method of controlling the behavior of a cell through modulation of the processing of an mRNA target by contacting the cell with an antisense compound acting via a non-cleavage event is disclosed in U.S. Pat. No. 6,210,892 and U.S. Pre-Grant Publication 20020049173.

Certain types of antisense compounds which specifically hybridize to the 5' cap region of their target mRNA can interfere with translation of the target mRNA into protein. Such oligomers include peptide-nucleic acid (PNA) oligomers, morpholino oligomers and oligonucleosides (such as those having an MMI or amide internucleoside linkage) and oligonucleotides having modifications at the 2' position of the sugar when such oligomers are targeted to the 5' cap region of their target mRNA. This is believed to occur via interference with ribosome assembly on the target mRNA. Methods for inhibiting the translation of a selected capped target mRNA by contacting target mRNA with an antisense compound are disclosed in U.S. Pat. No. 5,789,573.

Antisense compounds targeted to a specific poly(A) site of mRNA can be used to modulate the populations of alternatively polyadenylated transcripts. In addition, antisense compounds can be used to disrupt RNA regulatory structure thereby affecting, for example, the stability of the targeted RNA and its subsequent expression. Methods directed to such modulation are disclosed in U.S. Pat. No. 6,210,892 and Pre-Grant Publication 20020049173.

Compounds

The term "oligomeric compound" refers to a polymeric structure capable of hybridizing to a region of a nucleic acid molecule. This term includes oligonucleotides, oligonucleosides, oligonucleotide analogs, oligonucleotide mimetics and chimeric combinations of these. Oligomeric compounds are routinely prepared linearly but can be joined or otherwise prepared to be circular. Moreover, branched structures are known in the art. An "antisense compound" or "antisense oligomeric compound" refers to an oligomeric compound that is at least partially complementary to the region of a nucleic acid molecule to which it hybridizes and which modulates (increases or decreases) its expression. Consequently, while all antisense compounds can be said to be oligomeric compounds, not all oligomeric compounds are antisense compounds. An "antisense oligonucleotide" is an antisense compound that is a nucleic acid-based oligomer. An antisense oligonucleotide can be chemically modified. Nonlimiting examples of oligomeric compounds include primers, probes, antisense compounds, antisense oligonucleotides, external guide sequence (EGS) oligonucleotides and alternate splicers. In one embodiment, the oligomeric compound comprises an antisense strand hybridized to a sense strand. Oligomeric compounds can be introduced in the form of single-stranded, double-stranded, circular, branched or hairpins and can contain structural elements such as internal or terminal bulges or loops. Oligomeric double-stranded compounds can be two strands hybridized to form double-stranded compounds or a single strand with sufficient self complementarity to allow for hybridization and formation of a fully or partially double-stranded compound.

The oligomeric compounds provided herein comprise compounds from about 8 to about 80 nucleobases (i.e. from about 8 to about 80 linked nucleosides). One of ordinary skill in the art will appreciate that this comprehends antisense compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases.

In one embodiment, the antisense compounds provided herein comprise 13 to 80 nucleobases. One having ordinary skill in the art will appreciate that this embodies antisense compounds of 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases.

In one embodiment, the antisense compounds provided herein comprise 12 to 50 nucleobases. One having ordinary skill in the art will appreciate that this embodies antisense compounds of 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, or 50 nucleobases.

In one embodiment, the antisense compounds provided herein comprise 12 to 30 nucleobases. One having ordinary skill in the art will appreciate that this embodies antisense compounds of 12, 13, 14, 15, 16, 17, 18, 19, 20, 21, 22, 23, 24, 25, 26, 27, 28, 29 or 30 nucleobases.

In some embodiments, the antisense compounds provided herein comprise 15 to 30 nucleobases. One having ordinary skill in the art will appreciate that this embodies antisense compounds of 15, 16, 17, 18, 19, 20, 21, 22, 23, 24, 25, 26, 27, 28, 29 or 30 nucleobases.

In one embodiment, the antisense compounds provided herein comprise 20 to 30 nucleobases. One having ordinary skill in the art will appreciate that this embodies antisense compounds of 20, 21, 22, 23, 24, 25, 26, 27, 28, 29, or 30 nucleobases.

In one embodiment, the antisense compounds provided herein comprise 20 to 24 nucleobases. One having ordinary skill in the art will appreciate that this embodies antisense compounds of 20, 21, 22, 23, or 24 nucleobases.

In one embodiment, the antisense compounds provided herein comprise 16 to 20 nucleobases. One having ordinary skill in the art will appreciate that this embodies antisense compounds of 16, 17, 18, 19 or 20 nucleobases.

In one embodiment, the antisense compounds comprise 20 nucleobases.

In one embodiment, the antisense compounds comprise 19 nucleobases.

In one embodiment, the antisense compounds comprise 18 nucleobases.

In one embodiment, the antisense compounds comprise 17 nucleobases.

In one embodiment, the antisense compounds comprise 16 nucleobases.

In one embodiment, the antisense compounds comprise 15 nucleobases.

In one embodiment, the antisense compounds comprise 14 nucleobases.

In one embodiment, the antisense compounds comprise 13 nucleobases.

Antisense compounds 8-80 nucleobases in length, and any length within the range, comprising a stretch of at least eight (8) consecutive nucleobases selected from within the illustrative antisense compounds are considered to be suitable antisense compounds.

Compounds provided herein include oligonucleotide sequences that comprise at least the 8 consecutive nucleobases from the 5'-terminus of one of the illustrative antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80, or about 13 to about 80, or about 12 to about 50, or about 12 to about 30, or about 15 to about 30, or about 20 to about 30, or about 20 to about 24, or about 16 to about 20 nucleobases). Other compounds are represented by oligonucleotide sequences that comprise at least the 8 consecutive nucleobases from the 3'-terminus of one of the illustrative antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80, or about 13 to about 80, or about 12 to about 50, or about 12 to about 30, or about 15 to about 30, or about 20 to about 30, or about 20 to about 24, or about 16 to about 20 nucleobases). It is also understood that compounds may be represented by oligonucleotide sequences that comprise at least 8 consecutive nucleobases from an internal portion of the sequence of an illustrative compound, and may extend in either or both directions until the oligonucleotide contains about 8 to about 80, or about 13 to about 80, or about 12 to about 50, or about 12 to about 30, or about 15 to about 30, or about 20 to about 30, or about 20 to about 24, or about 16 to about 20 nucleobases.

In one embodiment, the compounds do not consist of the nucleobase sequence TGTTGTCATCCGCTGAGCCAT (SEQ ID NO: 93), AGGAGGTCAGCTGAGCAGCCA (SEQ ID NO: 94), CTTGTGGTGCTTGGCGTTCAT (SEQ ID NO: 95), GTAGGAAACATCCTTATGGGC (SEQ ID NO: 96), GATCCAGGGCCCCAAGTTGGG (SEQ ID NO: 97), GCTCTTGCAGGTGTAGGAGGT (SEQ ID NO: 98), TTCATTGCACAGAACAGTGGG (SEQ ID NO: 99), or CGCCACCTCCTCATTGGGGTT (SEQ ID NO: 100). In one embodiment, the compounds do not consist of the nucleobase sequence CTTGGCGTTCATGCAGACA (SEQ ID NO: 101), ATATAGGTAGGAAACATCC (SEQ ID NO: 102), CCATTGCTCACAGTCCTCT (SEQ ID NO: 103), GGAGTGAGTCCAGCCCACT (SEQ ID NO: 104). In one embodiment, the compounds do not comprise the nucleobase sequence TGTTGTCATCCGCTGAGCCAT (SEQ ID NO: 93), AGGAGGTCAGCTGAGCAGCCA (SEQ ID NO: 94), CTTGTGGTGCTTGGCGTTCAT (SEQ ID NO: 95), GTAGGAAACATCCTTATGGGC (SEQ ID NO: 96), GATCCAGGGCCCCAAGTTGGG (SEQ ID NO: 97), GCTCTTGCAGGTGTAGGAGGT (SEQ ID NO: 98), TTCATTGCACAGAACAGTGGG (SEQ ID NO: 99), or CGCCACCTCCTCATTGGGGTT (SEQ ID NO: 100). In one embodiment, the compounds do not comprise the nucleobase sequence CTTGGCGTTCATGCAGACA (SEQ ID NO: 101), ATATAGGTAGGAAACATCC (SEQ ID NO: 102), CCATTGCTCACAGTCCTCT (SEQ ID NO: 103), GGAGTGAGTCCAGCCCACT (SEQ ID NO: 104).

One having skill in the art armed with the antisense compounds illustrated herein will be able, without undue experimentation, to identify further antisense compounds.

Chemical Modifications

As is known in the art, a nucleoside is a base-sugar combination. The base portion of the nucleoside is normally a heterocyclic base (sometimes referred to as a "nucleobase" or simply a "base"). The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages

Specific examples of oligomeric compounds include oligonucleotides containing modified e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

Oligomeric compounds can have one or more modified internucleoside linkages. Modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, phosphonoacetate and thiophosphonoacetate (see Sheehan et al., *Nucleic Acids Research*, 2003, 31(14), 4109-4118 and Dellinger et al., *J. Am. Chem. Soc.*, 2003, 125, 940-950), selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage, i.e., a single inverted nucleoside residue which may be abasic (the nucleobase is missing or has a hydroxyl group in place thereof). Various salts, mixed salts and free acid forms are also included.

N3'-P5'-phosphoramidates have been reported to exhibit both a high affinity towards a complementary RNA strand and nuclease resistance (Gryaznov et al., *J. Am. Chem. Soc.*, 1994, 116, 3143-3144). N3'-P5'-phosphoramidates have been studied with some success in vivo to specifically down regulate the expression of the c-myc gene (Skorski et al., *Proc. Natl. Acad. Sci.*, 1997, 94, 3966-3971; and Faira et al., *Nat. Biotechnol.*, 2001, 19, 40-44).

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050.

In some embodiments, oligomeric compounds may have one or more phosphorothioate and/or heteroatom internucleoside linkages, in particular —$CH_2$—NH—O—$CH_2$—, —$CH_2$—N($CH_3$)—O—$CH_2$— (known as a methylene(methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleotide linkage is represented as —O—P(=O)(OH)—O—$CH_2$—). The MMI type internucleoside linkages are disclosed in the above referenced U.S. Pat. No. 5,489,677. Amide internucleoside linkages are disclosed in the above referenced U.S. Pat. No. 5,602,240.

Some oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439.

Modified Sugars

Oligomeric compounds may also contain one or more substituted sugar moieties. Suitable compounds can comprise one of the following at the 2' position: OH; F; O, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Also suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486-504), i.e., an alkoxyalkoxy group. A further modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylamino-ethoxy-ethyl or 2'-DMAEOE), i.e., 2'-O—$(CH_2)_2$—O—$(CH_2)_2$—N($CH_3$)$_2$, also described in examples hereinbelow.

Other modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. One 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Antisense compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; and, 6,147,200.

DNA-Like and RNA-Like Conformations

The terms used to describe the conformational geometry of homoduplex nucleic acids are "A Form" for RNA and "B Form" for DNA. In general, RNA:RNA duplexes are more stable and have higher melting temperatures (Tm's) than DNA:DNA duplexes (Sanger et al., *Principles of Nucleic Acid Structure,* 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger et al., *Principles of Nucleic Acid Structure,* 1984, Springer-Verlag; New York, N.Y.). As used herein, B-form geometry is inclusive of both C2'-endo pucker and O4'-endo pucker.

The structure of a hybrid duplex is intermediate between A- and B-form geometries, which may result in poor stacking interactions (Lane et al., *Eur. J. Biochem.,* 1993, 215, 297-306; Fedoroff et al., *J. Mol. Biol.,* 1993, 233, 509-523; Gonzalez et al., *Biochemistry,* 1995, 34, 4969-4982; Horton et al., *J. Mol. Biol.,* 1996, 264, 521-533). Consequently, compounds that favor an A-form geometry can enhance stacking interactions, thereby increasing the relative Tm and potentially enhancing a compound's antisense effect.

In one aspect, oligomeric compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA-like nucleosides so that particular properties of an oligomeric compound can be enhanced while maintaining the desirable 3'-endo conformational geometry.

There is an apparent preference for an RNA type duplex (A form helix, predominantly 3'-endo) as a requirement (e.g. trigger) of RNA interference which is supported in part by the fact that duplexes composed of 2'-deoxy-2'-F-nucleosides appears efficient in triggering RNAi response in the *C. elegans* system. Properties that are enhanced by using more stable 3'-endo nucleosides include but are not limited to: modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. Also provided herein are oligomeric triggers of RNAi having one or more nucleosides modified in such a way as to favor a C3'-endo type conformation.

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2'deoxy-2'F-nucleosides (Kawasaki et al., J. Med. Chem. (1993), 36, 831-841), which adopts the 3'-endo conformation positioning the electronegative fluorine atom in the axial position. Representative 2'-substituent groups amenable to the provided compounds are those that give A-form conformational properties (3'-endo) to the resultant duplexes include 2'-O-alkyl, 2'-O-substituted alkyl and 2'-fluoro substituent groups. Other suitable substituent groups are various alkyl and aryl ethers and thioethers, amines and monoalkyl and dialkyl substituted amines.

Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Along similar lines, triggers of RNAi response might be composed of one or more nucleosides modified in such a way that conformation is locked into a C3'-endo type conformation, i.e. Locked Nucleic Acid (LNA, Singh et al, Chem. Commun. (1998), 4, 455-456), and ethylene bridged Nucleic Acids (ENA™, Morita et al, Bioorganic & Medicinal Chemistry Letters (2002), 12, 73-76.)

It is further intended that multiple modifications can be made to one or more of the oligomeric compounds at multiple sites of one or more monomeric subunits (nucleosides are suitable) and or internucleoside linkages to enhance properties such as but not limited to activity in a selected application.

The synthesis of numerous of the modified nucleosides amenable to the provided compounds are known in the art (see for example, Chemistry of Nucleosides and Nucleotides Vol 1-3, ed. Leroy B. Townsend, 1988, Plenum press). The conformation of modified nucleosides and their oligomers can be estimated by various methods routine to those skilled in the art such as molecular dynamics calculations, nuclear magnetic resonance spectroscopy and CD measurements.

Oligonucleotide Mimetics

Another group of oligomeric compounds includes oligonucleotide mimetics. The term "mimetic" as it is applied to oligonucleotides includes oligomeric compounds wherein the furanose ring or the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid.

One such oligomeric compound, an oligonucleotide mimetic that has been shown to have excellent hybridization properties, is referred to as a peptide nucleic acid (PNA) (Nielsen et al., *Science,* 1991, 254, 1497-1500). PNAs have favorable hybridization properties, high biological stability and are electrostatically neutral molecules. PNA compounds have been used to correct aberrant splicing in a transgenic mouse model (Sazani et al., *Nat. Biotechnol.,* 2002, 20, 1228-1233). In PNA oligomeric compounds, the sugar-backbone of an oligonucleotide is replaced with an amide containing backbone, in particular an aminoethylglycine backbone. The nucleobases are bound directly or indirectly to aza nitrogen atoms of the amide portion of the backbone. Representative United States patents that teach the preparation of PNA oligomeric compounds include, but are not limited to, U.S. Pat. Nos. 5,539,082; 5,714,331; and 5,719,262. PNA compounds can be obtained commercially from Applied Biosystems (Foster City, Calif., USA). Numerous modifications to the basic PNA backbone are known in the art; particularly useful are PNA compounds with one or more amino acids conjugated to one or both termini. For example, 1-8 lysine or arginine residues are useful when conjugated to the end of a PNA molecule.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups have been selected to give a non-ionic oligomeric compound. Morpholino-based oligomeric compounds are non-ionic mimetics of oligonucleotides which are less likely to form undesired interactions with cellular proteins (Dwaine A. Braasch and David R. Corey, *Biochemistry*, 2002, 41(14), 4503-4510). Morpholino-based oligomeric compounds have been studied in zebrafish embryos (see: *Genesis*, volume 30, issue 3, 2001 and Heasman, J., *Dev. Biol.*, 2002, 243, 209-214). Further studies of morpholino-based oligomeric compounds have also been reported (Nasevicius et al., *Nat. Genet.*, 2000, 26, 216-220; and Lacerra et al., *Proc. Natl. Acad. Sci.*, 2000, 97, 9591-9596). Morpholino-based oligomeric compounds are disclosed in U.S. Pat. No. 5,034,506. The morpholino class of oligomeric compounds has been prepared with a variety of different linking groups joining the monomeric subunits. Linking groups can be varied from chiral to achiral, and from charged to neutral. U.S. Pat. No. 5,166,315 discloses linkages including —O—P(=O)(N(CH$_3$)$_2$)—O—; U.S. Pat. No. 5,034,506 discloses achiral intermorpholino linkages; and U.S. Pat. No. 5,185,444 discloses phosphorus containing chiral intermorpholino linkages.

A further class of oligonucleotide mimetic is referred to as cyclohexene nucleic acids (CeNA). In CeNA oligonucleotides, the furanose ring normally present in a DNA or RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (Wang et al., *J. Am. Chem. Soc.*, 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate *E. coli* RNase H resulting in cleavage of the target RNA strand.

A further modification includes bicyclic sugar moieties such as "Locked Nucleic Acids" (LNAs) in which the 2'-hydroxyl group of the ribosyl sugar ring is linked to the 4' carbon atom of the sugar ring thereby forming a 2'-C,4'-C-oxymethylene linkage to form the bicyclic sugar moiety (reviewed in Elayadi et al., *Curr. Opinion Invens. Drugs*, 2001, 2, 558-561; Braasch et al., *Chem. Biol.*, 2001, 8 1-7; and Orum et al., *Curr. Opinion Mol. Ther.*, 2001, 3, 239-243; see also U.S. Pat. Nos. 6,268,490 and 6,670,461). The linkage can be a methylene (—CH$_2$—) group bridging the 2' oxygen atom and the 4' carbon atom, for which the term LNA is used for the bicyclic moiety; in the case of an ethylene group in this position, the term ENA™ is used (Singh et al., Chem. Commun., 1998, 4, 455-456; ENA™: Morita et al., *Bioorganic Medicinal Chemistry*, 2003, 11, 2211-2226). LNA and other bicyclic sugar analogs display very high duplex thermal stabilities with complementary DNA and RNA (Tm=+3 to +10° C.), stability towards 3'-exonucleolytic degradation and good solubility properties. LNA's are commercially available from ProLigo (Paris, France and Boulder, Colo., USA).

An isomer of LNA that has also been studied is alpha-L-LNA which has been shown to have superior stability against a 3'-exonuclease. The alpha-L-LNA's were incorporated into antisense gapmers and chimeras that showed potent antisense activity (Frieden et al., *Nucleic Acids Research*, 2003, 21, 6365-6372).

Another similar bicyclic sugar moiety that has been prepared and studied has the bridge going from the 3'-hydroxyl group via a single methylene group to the 4' carbon atom of the sugar ring thereby forming a 3'-C,4'-C-oxymethylene linkage (see U.S. Pat. No. 6,043,060).

LNA has been shown to form exceedingly stable LNA:LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11° C.) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands. DNA-LNA chimeras have been shown to efficiently inhibit gene expression when targeted to a variety of regions (5'-untranslated region, region of the start codon or coding region) within the luciferase mRNA (Braasch et al., *Nucleic Acids Research*, 2002, 30, 5160-5167).

Potent and nontoxic antisense oligonucleotides containing LNAs have been described (Wahlestedt et al., *Proc. Natl. Acad. Sci. U.S.A.*, 2000, 97, 5633-5638). The authors have demonstrated that LNAs confer several desired properties. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in *Escherichia coli*. Lipofectin-mediated efficient delivery of LNA into living human breast cancer cells has also been accomplished. Further successful in vivo studies involving LNA's have shown knock-down of the rat delta opioid receptor without toxicity (Wahlestedt et al., *Proc. Natl. Acad. Sci.*, 2000, 97, 5633-5638) and in another study showed a blockage of the translation of the large subunit of RNA polymerase II (Fluiter et al., *Nucleic Acids Res.*, 2003, 31, 953-962).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., WO 99/14226). Furthermore, synthesis of 2'-amino-LNA, a novel conformationally restricted high-affinity oligonucleotide analog has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Another oligonucleotide mimetic that has been prepared and studied is threose nucleic acid. This oligonucleotide mimetic is based on threose nucleosides instead of ribose nucleosides. Initial interest in (3',2')-alpha-L-threose nucleic acid (TNA) was directed to the question of whether a DNA polymerase existed that would copy the TNA. It was found that certain DNA polymerases are able to copy limited stretches of a TNA template (reported in *Chemical and Engineering News*, 2003, 81, 9). In another study it was determined that TNA is capable of antiparallel Watson-Crick base pairing with complementary DNA, RNA and TNA oligonucleotides (Chaput et al., *J. Am. Chem. Soc.*, 2003, 125, 856-857).

In one study (3',2')-alpha-L-threose nucleic acid was prepared and compared to the 2' and 3' amidate analogs (Wu et al., *Organic Letters*, 2002, 4(8), 1279-1282). The amidate analogs were shown to bind to RNA and DNA with comparable strength to that of RNA/DNA.

Further oligonucleotide mimetics have been prepared to include bicyclic and tricyclic nucleoside analogs (see Steffens et al., *Helv. Chim. Acta*, 1997, 80, 2426-2439; Steffens et al., *J. Am. Chem. Soc.*, 1999, 121, 3249-3255; Renneberg et al., *J. Am. Chem. Soc.*, 2002, 124, 5993-6002; and Renneberg et al., *Nucleic acids res.*, 2002, 30, 2751-2757). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids which incorporate a phosphorus group in the backbone. This class of oligonucleotide mimetic is reported to have useful physical and biological and pharmacological properties in the areas of inhibiting gene expression (antisense oligonucleotides, sense oligonucleotides and triplex-forming oligonucleotides), as probes for the detection of nucleic acids and as auxiliaries for use in molecular biology. Further oligonucleotide mimetics amenable to the provided compounds have been prepared wherein a cyclobutyl ring replaces the naturally occurring furanosyl ring.

Modified and Alternate Nucleobases

Oligomeric compounds can also include nucleobase (often referred to in the art as heterocyclic base or simply as "base") modifications or substitutions. As used herein, "unmodified" or "natural" nucleobases include the purine bases adenine (A) and guanine (G), and the pyrimidine bases thymine (T), cytosine (C) and uracil (U). A "substitution" is the replacement of an unmodified or natural base with another unmodified or natural base. "Modified" nucleobases mean other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-b)(1,4)benzoxazin-2 (3H)-one), carbazole cytidine (2H-pyrimido(4,5-b)indol-2-one), pyridoindole cytidine (H-pyrido(3',2':4,5)pyrrolo(2,3-d)pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are known to those skilled in the art as suitable for increasing the binding affinity of the provided compounds. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently suitable base substitutions, even more particularly when combined with 2'-O-methoxyethyl sugar modifications. It is understood in the art that modification of the base does not entail such chemical modifications as to produce substitutions in a nucleic acid sequence.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,681,941; and 5,750,692.

Oligomeric compounds can also include polycyclic heterocyclic compounds in place of one or more of the naturally-occurring heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Representative cytosine analogs that make 3 hydrogen bonds with a guanosine in a second strand include 1,3-diazaphenoxazine-2-one (Kurchavov, et al., *Nucleosides and Nucleotides*, 1997, 16, 1837-1846), 1,3-diazaphenothiazine-2-one, (Lin, K.-Y.; Jones, R. J.; Matteucci, M. J. Am. Chem. Soc. 1995, 117, 3873-3874) and 6,7,8,9-tetrafluoro-1,3-diazaphenoxazine-2-one (Wang, J.; Lin, K.-Y., Matteucci, M. Tetrahedron Lett. 1998, 39, 8385-8388). Incorporated into oligonucleotides these base modifications were shown to hybridize with complementary guanine and the latter was also shown to hybridize with adenine and to enhance helical thermal stability by extended stacking interactions (also see U.S. Pre-Grant Publications 20030207804 and 20030175906).

Further helix-stabilizing properties have been observed when a cytosine analog/substitute has an aminoethoxy moiety attached to the rigid 1,3-diazaphenoxazine-2-one scaffold (Lin, K.-Y.; Matteucci, M. J. Am. Chem. Soc. 1998, 120, 8531-8532). Binding studies demonstrated that a single incorporation could enhance the binding affinity of a model oligonucleotide to its complementary target DNA or RNA with a $\Delta T_m$ of up to 18° C. relative to 5-methyl cytosine ($dC5^{me}$), which is a high affinity enhancement for a single modification. On the other hand, the gain in helical stability does not compromise the specificity of the oligonucleotides.

Further tricyclic heterocyclic compounds and methods of using them that are amenable to use with the provided compounds are disclosed in U.S. Pat. Nos. 6,028,183, and 6,007,992.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNase H, enhance cellular uptake and exhibit an increased antisense activity (Lin, K-Y; Matteucci, M. J. Am. Chem. Soc. 1998, 120, 8531-8532). The activity enhancement was even more pronounced in case of G-clamp, as a single substitution was shown to significantly improve the in vitro potency of a 20 mer 2'-deoxyphosphorothioate oligonucleotides (Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518).

Further modified polycyclic heterocyclic compounds useful as heterocyclic bases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,750,692; 5,830,653; 5,763,588; 6,005,096; and 5,681,941, and U.S. Pre-Grant Publication 20030158403.

Conjugates

Another modification of the oligomeric compounds involves chemically linking to the oligomeric compound one or more moieties or conjugates which enhance the properties of the oligomeric compound, such as to enhance the activity, cellular distribution or cellular uptake of the oligomeric compound. These moieties or conjugates can include conjugate groups covalently bound to functional groups such as primary or secondary hydroxyl groups. Conjugate groups include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this disclosure, include groups that improve uptake, enhance resistance to degradation, and/or strengthen sequence-specific hybridization with the target nucleic acid. Groups that enhance the pharmacokinetic properties, in the context of this disclosure, include groups that improve uptake, distribution, metabolism or excretion of the compounds. Representative conjugate groups are disclosed in International Patent Application PCT/US92/09196, filed Oct. 23, 1992, and U.S. Pat. Nos. 6,287,860 and 6,762,169.

Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylaminocarbonyl-oxycholesterol moiety. Oligomeric compounds may also be conjugated to drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. Pat. No. 6,656,730.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Oligomeric compounds can also be modified to have one or more stabilizing groups that are generally attached to one or both termini of an oligomeric compound to enhance properties such as for example nuclease stability. Included in stabilizing groups are cap structures. By "cap structure or terminal cap moiety" is meant chemical modifications, which have been incorporated at either terminus of oligonucleotides (see for example Wincott et al., WO 97/26270). These terminal modifications protect the oligomeric compounds having terminal nucleic acid molecules from exonuclease degradation, and can improve delivery and/or localization within a cell. The cap can be present at either the 5'-terminus (5'-cap) or at the 3'-terminus (3'-cap) or can be present on both termini of a single strand, or one or more termini of both strands of a double-stranded compound. This cap structure is not to be confused with the inverted methylguanosine "5'cap" present at the 5' end of native mRNA molecules. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270). For siRNA constructs, the 5' end (5' cap) is commonly but not limited to 5'-hydroxyl or 5'-phosphate.

Particularly suitable 3'-cap structures include, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925).

Further 3' and 5'-stabilizing groups that can be used to cap one or both ends of an oligomeric compound to impart nuclease stability include those disclosed in WO 03/004602 published on Jan. 16, 2003.

Chimeric Compounds

It is not necessary for all positions in a given oligomeric compound to be uniformly modified, and in fact more than one of the aforementioned modifications may be incorporated in a single compound or even within a single nucleoside within an oligomeric compound.

The present disclosure also includes oligomeric compounds which are chimeric compounds. "Chimeric" oligomeric compounds or "chimeras," as used herein, are single- or double-stranded oligomeric compounds, such as oligonucleotides, which contain two or more chemically distinct regions, each comprising at least one monomer unit, i.e., a nucleotide in the case of an oligonucleotide compound. Chimeric antisense oligonucleotides are one form of oligomeric compound. These oligonucleotides typically contain at least one region which is modified so as to confer upon the oligonucleotide increased resistance to nuclease degradation, increased cellular uptake, alteration of charge, increased stability and/or increased binding affinity for the target nucleic acid. An additional region of the oligonucleotide may serve as a substrate for RNAses or other enzymes. By way of example, RNAse H is a cellular endonuclease which cleaves the RNA strand of an RNA:DNA duplex. Activation of RNase H, therefore, results in cleavage of the RNA target when bound by a DNA-like oligomeric compound, thereby greatly enhancing the efficiency of oligonucleotide-mediated inhibition of gene expression. The cleavage of RNA:RNA hybrids can, in like fashion, be accomplished through the actions of endoribonucleases, such as RNase III or RNAseL which cleaves both cellular and viral RNA. Cleavage products of the RNA target can be routinely detected by gel electrophoresis and, if necessary, associated nucleic acid hybridization techniques known in the art.

Chimeric oligomeric compounds can be formed as composite structures of two or more oligonucleotides, modified oligonucleotides, oligonucleosides, oligonucleotide mimetics, or regions or portions thereof. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922.

A "gapmer" is defined as an oligomeric compound, generally an oligonucleotide, having a 2'-deoxyoligonucleotide region flanked by non-deoxyoligonucleotide segments. The central region is referred to as the "gap." The flanking segments are referred to as "wings." While not wishing to be bound by theory, the gap of the gapmer presents a substrate recognizable by RNase H when bound to the RNA target whereas the wings do not provide such a substrate but can confer other properties such as contributing to duplex stability or advantageous pharmacokinetic effects. Each wing can be one or more non-deoxyoligonucleotide monomers (if one of the wings has zero non-deoxyoligonucleotide monomers, a "hemimer" is described). In one embodiment, the gapmer is a ten deoxynucleotide gap flanked by five non-deoxynucleotide wings. This is referred to as a 5-10-5 gapmer. Other configurations are readily recognized by those skilled in the art. In one embodiment the wings comprise 2'-MOE modified nucleotides. In another embodiment the gapmer has a phosphorothioate backbone. In another embodiment the gapmer has 2'-MOE wings and a phosphorothioate backbone. Other suitable modifications are readily recognizable by those skilled in the art.

Oligomer Synthesis

Oligomerization of modified and unmodified nucleosides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Oligomeric compounds can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Precursor Compounds

The following precursor compounds, including amidites and their intermediates can be prepared by methods routine to those skilled in the art; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, (5'-O-(4,4'-Dimethoxytriphenylmethyl)-2'-deoxy-N$^4$-benzoyl-5-methylcytidin-3'-O-yl)-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, (5'-O-(4,4'-Dimethoxytriphenylmethyl)-2'-O-(2-methoxyethyl)-5-methyluridin-3'-O-yl)-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-N$^4$-benzoyl-5-methylcytidine penultimate intermediate, (5'-O-(4,4'-Dimethoxytriphenylmethyl)-2'-O-(2-methoxyethyl)-N$^4$-benzoyl-5-methylcytidin-3'-O-yl)-2-cyanoethyl-N,N-diisopropylphosphoramidite (MOE 5-Me-C amidite), (5'-O-(4,4'-Dimethoxytriphenylmethyl)-2'-O-(2-methoxyethyl)-N$^6$-benzoyladenosin-3'-O-yl)-2-cyanoethyl-N,N-diisopropylphosphoramidite (MOE A amidite), (5'-O-(4,4'-Dimethoxytriphenylmethyl)-2'-O-(2-methoxyethyl)-N$^4$-isobutyrylguanosin-3'-O-yl)-2-cyanoethyl-N,N-diisopropylphosphoramidite (MOE G amidite), 2'-O-(Aminooxyethyl) nucleoside amidites and 2'-O-(dimethylaminooxyethyl) nucleoside amidites, 2'-(Dimethylaminooxyethoxy) nucleoside amidites, 5'-O-tert-Butyldiphenylsilyl-O$^2$-2'-anhydro-5-methyluridine, 5'-O-tert-Butyldiphenylsilyl-2'-O-(2-hydroxyethyl)-5-methyluridine, 2'-O-((2-phthalimidoxy)ethyl)-5'-t-butyldiphenylsilyl-5-methyluridine, 5'-O-tert-butyldiphenylsilyl-2'-O-((2-formadoximinooxy)ethyl)-5-methyluridine, 5'-O-tert-Butyldiphenylsilyl-2'-O-(N,N dimethylaminooxyethyl)-5-methyluridine, 2'-O-dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-((2-cyanoethyl)-N,N-diisopropylphosphoramidite), 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-((2-cyanoethyl)-N,N-diisopropylphosphoramidite), 2'-dimethylaminoethoxyethoxy (2'-DMAEOE) nucleoside amidites, 2'-O-(2(2-N,N-dimethylaminoethoxy)ethyl)-5-methyl uridine, 5'-O-dimethoxytrityl-2'-O-(2(2-N,N-dimethylaminoethoxy)-ethyl))-5-methyl uridine and 5'-O-Dimethoxytrityl-2'-O-(2(2-N,N-dimethylaminoethoxy)-ethyl))-5-methyluridine-3'-O-(cyanoethyl-N,N-diisopropyl) phosphoramidite.

The preparation of such precursor compounds for oligonucleotide synthesis are routine in the art and disclosed in U.S. Pat. No. 6,426,220 and published PCT WO 02/36743.

2'-Deoxy and 2'-methoxy beta-cyanoethyldiisopropyl phosphoramidites can be purchased from commercial sources (e.g. Chemgenes, Needham, Mass. or Glen Research, Inc. Sterling, Va.). Other 2'-O-alkoxy substituted nucleoside amidites can be prepared as described in U.S. Pat. No. 5,506,351.

Oligonucleotides containing 5-methyl-2'-deoxycytidine (5-Me-C) nucleotides can be synthesized routinely according to published methods (Sanghvi, et. al., *Nucleic Acids Research*, 1993, 21, 3197-3203) using commercially available phosphoramidites (Glen Research, Sterling Va. or ChemGenes, Needham, Mass.).

2'-fluoro oligonucleotides can be synthesized routinely as described (Kawasaki, et. al., *J. Med. Chem.*, 1993, 36, 831-841) and U.S. Pat. No. 5,670,633.

2'-O-Methoxyethyl-substituted nucleoside amidites can be prepared routinely as per the methods of Martin, P., *Helvetica Chimica Acta*, 1995, 78, 486-504.

Aminooxyethyl and dimethylaminooxyethyl amidites can be prepared routinely as per the methods of U.S. Pat. No. 6,127,533.

Oligonucleotide Synthesis

Phosphorothioate-containing oligonucleotides (P=S) can be synthesized by methods routine to those skilled in the art (see, for example, Protocols for Oligonucleotides and Analogs, Ed. Agrawal (1993), Humana Press). Phosphinate oligonucleotides can be prepared as described in U.S. Pat. No. 5,508,270.

Alkyl phosphonate oligonucleotides can be prepared as described in U.S. Pat. No. 4,469,863.

3'-Deoxy-3'-methylene phosphonate oligonucleotides can be prepared as described in U.S. Pat. No. 5,610,289 or 5,625,050.

Phosphoramidite oligonucleotides can be prepared as described in U.S. Pat. No. 5,256,775 or U.S. Pat. No. 5,366,878.

Alkylphosphonothioate oligonucleotides can be prepared as described in published PCT applications PCT/US94/00902 and PCT/US93/06976 (published as WO 94/17093 and WO 94/02499, respectively).

3'-Deoxy-3'-amino phosphoramidate oligonucleotides can be prepared as described in U.S. Pat. No. 5,476,925.

Phosphotriester oligonucleotides can be prepared as described in U.S. Pat. No. 5,023,243.

Borano phosphate oligonucleotides can be prepared as described in U.S. Pat. Nos. 5,130,302 and 5,177,198.

4'-thio-containing oligonucleotides can be synthesized as described in U.S. Pat. No. 5,639,873.

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal linked oligonucleosides can be prepared as described in U.S. Pat. Nos. 5,264,562 and 5,264,564.

Ethylene oxide linked oligonucleosides can be prepared as described in U.S. Pat. No. 5,223,618.

Peptide Nucleic Acid Synthesis

Peptide nucleic acids (PNAs) can be prepared in accordance with any of the various procedures referred to in Peptide Nucleic Acids (PNA): Synthesis, Properties and Potential Applications, *Bioorganic & Medicinal Chemistry*, 1996, 4, 5-23. They may also be prepared in accordance with U.S. Pat. Nos. 5,539,082, 5,700,922, 5,719,262, 6,559,279 and 6,762,281.

Synthesis of 2'-O-Protected Oligomers/RNA Synthesis

Oligomeric compounds incorporating at least one 2'-O-protected nucleoside by methods routine in the art. After incorporation and appropriate deprotection the 2'-O-protected nucleoside will be converted to a ribonucleoside at the position of incorporation. The number and position of the 2-ribonucleoside units in the final oligomeric compound can vary from one at any site or the strategy can be used to prepare up to a full 2'-OH modified oligomeric compound.

A large number of 2'-O-protecting groups have been used for the synthesis of oligoribonucleotides and any can be used. Some of the protecting groups used initially for oligoribonucleotide synthesis included tetrahydropyran-1-yl and 4-methoxytetrahydropyran-4-yl. These two groups are not compatible with all 5'-O-protecting groups so modified versions were used with 5'-DMT groups such as 1-(2-fluorophenyl)-4-methoxypiperidin-4-yl (Fpmp). Reese et al. have identified a number of piperidine derivatives (like Fpmp) that are useful in the synthesis of oligoribonucleotides including 1-[(chloro-4-methyl)phenyl]-4'-methoxypiperidin-4-yl (Reese et al., Tetrahedron Lett., 1986, (27), 2291). Another approach is to replace the standard 5'-DMT (dimethoxytrityl) group with protecting groups that were removed under non-acidic conditions such as levulinyl and 9-fluorenylmethoxycarbonyl. Such groups enable the use of acid labile 2'-protecting groups for oligoribonucleotide synthesis. Another more widely used protecting group, initially used for the synthesis of oligoribonucleotides, is the t-butyldimethylsilyl group (Ogilvie et al., Tetrahedron Lett., 1974, 2861; Hakimelahi et al., Tetrahedron Lett., 1981, (22), 2543; and Jones et al., J. Chem. Soc. Perkin I., 2762). The 2'-O-protecting groups can require special reagents for their removal. For example, the t-butyldimethylsilyl group is normally removed after all other cleaving/deprotecting steps by treatment of the oligomeric compound with tetrabutylammonium fluoride (TBAF).

One group of researchers examined a number of 2'-O-protecting groups (Pitsch, S., Chimia, 2001, (55), 320-324.) The group examined fluoride labile and photolabile protecting groups that are removed using moderate conditions. One photolabile group that was examined was the [2-(nitrobenzyl)oxy]methyl (nbm) protecting group (Schwartz et al., Bioorg. Med. Chem. Lett., 1992, (2), 1019.) Other groups examined included a number structurally related formaldehyde acetal-derived, 2'-O-protecting groups. Also prepared were a number of related protecting groups for preparing 2'-O-alkylated nucleoside phosphoramidites including 2'-O-[(triisopropylsilyl)oxy]methyl (2'-O—CH$_2$—O—Si(iPr)$_3$, TOM). One 2'-O-protecting group that was prepared to be used orthogonally to the TOM group was 2'-O—[(R)-1-(2-nitrophenyl)ethyloxy)methyl] ((R)-mnbm).

Another strategy using a fluoride labile 5'-O-protecting group (non-acid labile) and an acid labile 2'-O-protecting group has been reported (Scaringe, Stephen A., Methods, 2001, (23) 206-217). A number of possible silyl ethers were examined for 5'-O-protection and a number of acetals and orthoesters were examined for 2'-O-protection. The protection scheme that gave the best results was 5'-O-silyl ether-2'-ACE (5'-O-bis(trimethylsiloxy)cyclododecyloxysilyl ether (DOD)-2'-O-bis(2-acetoxyethoxy)methyl (ACE). This approach uses a modified phosphoramidite synthesis approach in that some different reagents are required that are not routinely used for RNA/DNA synthesis.

The main RNA synthesis strategies that are presently being used commercially include 5'-O-DMT-2'-O-t-butyldimethylsilyl (TBDMS), 5'-DMT-2'-O-[1(2-fluorophenyl)-4-methoxypiperidin-4-yl] (FPMP), 2'-O-[(triisopropylsilyl)oxy]methyl (2'-O—CH$_2$—O—Si(iPr)$_3$ (TOM), and the 5'-O-silyl ether-2'-ACE (5'-O-bis(trimethylsiloxy)cyclododecyloxysilyl ether (DOD)-2'-O-bis(2-acetoxyethoxy)methyl (ACE). Some companies currently offering RNA products include Pierce Nucleic Acid Technologies (Milwaukee, Wis.), Dharmacon Research Inc. (a subsidiary of Fisher Scientific, Lafayette, Colo.), and Integrated DNA Technologies, Inc. (Coralville, Iowa). One company, Princeton Separations, markets an RNA synthesis activator advertised to reduce coupling times especially with TOM and TBDMS chemistries. Such an activator would also be amenable to the provided oligomeric compounds.

All of the aforementioned RNA synthesis strategies are amenable to the oligomeric compounds provided herein. Strategies that would be a hybrid of the above e.g. using a 5'-protecting group from one strategy with a 2'-O-protecting from another strategy is also contemplated herein.

Synthesis of Chimeric Oligomeric Compounds (2'-O-Me)-(2'-deoxy)-(2'-O-Me) Chimeric Phosphorothioate Oligonucleotides Chimeric oligonucleotides having 2'-O-alkyl phosphorothioate and 2'-deoxy phosphorothioate oligonucleotide segments can be routinely synthesized by one skilled in the art, using, for example, an Applied Biosystems automated DNA synthesizer Model 394. Oligonucleotides can be synthesized using an automated synthesizer and 2'-deoxy-5'-dimethoxytrityl-3'-O-phosphoramidite for the DNA portion and 5'-dimethoxytrityl-2'-O-methyl-3'-O-phosphoramidite for the 2'-O-alkyl portion. In one nonlimiting example, the standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia (NH$_4$OH) for 12-16 hr at 55° C. The deprotected oligonucleotide is then recovered by an appropriate method (precipitation, column chromatography, volume reduced in vacuo) and analyzed by methods routine in the art.

(2'-O-(2-Methoxyethyl))-(2'-deoxy)-(2'-O-(2-Methoxyethyl)) Chimeric Phosphorothioate Oligonucleotides (2'-O-(2-methoxyethyl))-(2'-deoxy)-(-2'-O-(2-methoxyethyl)) chimeric phosphorothioate oligonucleotides can be prepared as per the procedure above for the 2'-O-methyl chimeric oligonucleotide, with the substitution of 2'-O-(methoxyethyl) amidites for the 2'-O-methyl amidites.

(2'-O-(2-Methoxyethyl)Phosphodiester)-(2'-deoxy Phosphorothioate)-(2'-O-(2-Methoxyethyl)Phosphodiester) Chimeric Oligonucleotides (2'-O-(2-methoxyethyl phosphodiester)-(2'-deoxy phosphorothioate)-(2'-O-(methoxyethyl)phosphodiester) chimeric oligonucleotides can be prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides can be synthesized according to U.S. Pat. No. 5,623,065.

Oligomer Purification and Analysis

Methods of oligonucleotide purification and analysis are known to those skilled in the art. Analysis methods include capillary electrophoresis (CE) and electrospray-mass spectroscopy. Such synthesis and analysis methods can be performed in multi-well plates.

Hybridization

"Hybridization" means the pairing of complementary strands of oligomeric compounds. While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An oligomeric compound is specifically hybridizable when there is a sufficient degree of complementarity to avoid non-specific binding of the oligomeric compound to non-target nucleic acid sequences under conditions in which specific binding is desired, i.e., under physiological conditions in the case of in vivo assays or therapeutic treatment, and under conditions in which assays are performed in the case of in vitro assays.

"Stringent hybridization conditions" or "stringent conditions" refer to conditions under which an oligomeric compound will hybridize to its target sequence, but to a minimal number of other sequences. Stringent conditions are sequence-dependent and will be different in different circumstances, and "stringent conditions" under which oligomeric compounds hybridize to a target sequence are determined by the nature and composition of the oligomeric compounds and the assays in which they are being investigated.

Complementarity

"Complementarity," as used herein, refers to the capacity for precise pairing between two nucleobases on one or two oligomeric compound strands. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be a complementary position. The oligomeric compound and the further DNA or RNA are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligomeric compound and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oligomeric compounds provided herein comprise at least 70%, or at least 75%, or at least 80%, or at least 85%, or at least 90%, or at least 92%, or at least 95%, or at least 97%, or at least 98%, or at least 99% sequence complementarity to a target region within the target nucleic acid sequence to which they are targeted. For example, an oligomeric compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the oligomeric compounds provided herein. Percent complementarity of an oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

Oligomeric compounds, or a portion thereof, may have a defined percent identity to a SEQ ID NO, or a compound having a specific ISIS number. This identity may be over the entire length of the oligomeric compound, or in a portion of the oligomeric compound (e.g., nucleobases 1-20 of a 27-mer may be compared to a 20-mer to determine percent identity of the oligomeric compound to the SEQ ID NO) It is understood by those skilled in the art that an oligonucleotide need not have an identical sequence to those described herein to function similarly to the oligonucleotides described herein. Shortened (i.e., deleted, and therefore non-identical) versions of oligonucleotides taught herein, or non-identical (i.e., one base replaced with another) versions of the oligonucleotides taught herein fall within the scope of the disclosure. Percent identity is calculated according to the number of bases that are identical to the SEQ ID NO or compound to which it is being compared. The non-identical bases may be adjacent to each other, dispersed through out the oligonucleotide, or both.

For example, a 16-mer having the same sequence as nucleobases 2-17 of a 20-mer is 80% identical to the 20-mer. Alternatively, a 20-mer containing four nucleobases not identical to the 20-mer is also 80% identical to the 20-mer. A 14-mer having the same sequence as nucleobases 1-14 of an 18-mer is 78% identical to the 18-mer. Such calculations are well within the ability of those skilled in the art.

The percent identity is based on the percent of nucleobases in the original sequence present in a portion of the modified sequence. Therefore, a 30 nucleobase oligonucleotide comprising the full sequence of a 20 nucleobase SEQ ID NO would have a portion of 100% identity with the 20 nucleobase SEQ ID NO while further comprising an additional 10 nucleobase portion. As described herein, the full length of the modified sequence may constitute a single portion.

The oligomeric compounds of the also include compounds in which a different base is present at one or more of the nucleotide positions in the compound. For example, if the first nucleotide is an adenosine, compounds may be produced which contain thymidine, guanosine or cytidine at this position. This may be done at any of the positions of the oligomeric compound. These compounds are then tested using the methods described herein to determine their ability to inhibit expression of FR-alpha mRNA.

Target Nucleic Acids

"Targeting" an oligomeric compound to a particular target nucleic acid molecule can be a multistep process. The process usually begins with the identification of a target nucleic acid whose expression is to be modulated. As used herein, the terms "target nucleic acid" and "nucleic acid encoding FR-alpha" encompass DNA encoding FR-alpha, RNA (including pre-mRNA and mRNA) transcribed from such DNA, and also cDNA derived from such RNA. For example, the target nucleic acid can be a cellular gene (or mRNA transcribed from the gene) whose expression is associated with a particular disorder or disease state, or a nucleic acid molecule from an infectious agent. As disclosed herein, the target nucleic acid encodes FR-alpha.

Target Regions, Segments, and Sites

The targeting process usually also includes determination of at least one target region, segment, or site within the target nucleic acid for the antisense interaction to occur such that the desired effect, e.g., modulation of expression, will result. "Region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used herein, are defined as unique nucleobase positions within a target nucleic acid.

Start Codons

Since, as is known in the art, the translation initiation codon is typically 5' AUG (in transcribed mRNA molecules; 5' ATG in the corresponding DNA molecule), the translation initiation codon is also referred to as the "AUG codon," the "start codon" or the "AUG start codon." A minority of genes have a translation initiation codon having the RNA sequence 5' GUG, 5' UUG or 5' CUG, and 5' AUA, 5' ACG and 5' CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. "Start codon" and "translation initiation codon" refer to the codon or codons that are used in vivo to initiate translation of an mRNA transcribed from a gene encoding a protein, regardless of the sequence(s) of such codons. It is also known in the art that a translation termination codon (or "stop codon") of a gene may have one of three sequences, i.e., 5' UAA, 5' UAG and 5' UGA (the corresponding DNA sequences are 5' TAA, 5' TAG and 5' TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with oligomeric compounds.

Coding Regions

The open reading frame (ORF) or "coding region," which is known in the art to refer to the region between the translation initiation codon and the translation termination codon, is also a region which may be targeted effectively. As used herein, one region is the intragenic region encompassing the translation initiation or termination codon of the open reading frame (ORF) of a gene.

Untranslated Regions

Other target regions include the 5' untranslated region (5'UTR), known in the art to refer to the portion of an mRNA in the 5' directions from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. The 5' cap region is also a target.

Introns and Exons

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence, resulting in exon-exon junctions at the site where exons are joined. Targeting exon-exon junctions can be useful in situations where aberrant levels of a normal splice product are implicated in disease, or where aberrant levels of an aberrant splice product are implicated in disease. Targeting splice sites, i.e., intron-exon junctions or exon-intron junctions can also be particularly useful in situations where aberrant splicing is implicated in disease, or where an overproduction of a particular splice product is implicated in disease. Aberrant fusion junctions due to rearrangements or deletions are also suitable targets. mRNA transcripts produced via the process of splicing of two (or more) mRNAs from different gene sources are known as "fusion transcripts" and are also suitable targets. It is also known that introns can be effectively targeted using antisense compounds targeted to, for example, DNA or pre-mRNA. Single-stranded antisense compounds such as oligonucleotide compounds that work via an RNase H mechanism are effective for targeting pre-mRNA. Antisense compounds that function via an occupancy-based mechanism are effective for redirecting splicing as they do not, for example, elicit RNase H cleavage of the mRNA, but rather leave the mRNA intact and promote the yield of desired splice product(s).

Variants

It is also known in the art that alternative RNA transcripts can be produced from the same genomic region of DNA. These alternative transcripts are generally known as "variants." More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants." Consequently, mRNA variants are processed pre-mRNA variants and each unique pre-mRNA variant must always produce a unique mRNA variant as a result of splicing. These mRNA variants are also known as "alternative splice variants." If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Consequently, the types of variants described herein are also suitable target nucleic acids.

Target Names and Synonyms

In accordance with the present disclosure are compositions and methods for modulating the expression of FR-alpha (also known as folate receptor 1 (adult); FBP; FOLR; FOLR1; and MOv18). Listed in Table 1 are GENBANK® accession numbers used to design oligomeric compounds targeted to FR-alpha.

TABLE 1

Gene Target Sequences

| Species | Genbank # | SEQ ID NO |
|---|---|---|
| Human | NM_000802.2 | 1 |
| Human | NM_016724.1 | 2 |
| Human | NM_016725.1 | 3 |
| Human | NM_016729.1 | 4 |
| Human | NM_016730.1 | 5 |
| Human | NM_016731.2 | 6 |
| Human | nucleotides 2122000 to 2132000 of NT_033927.7 | 7 |

Modulation of Target Expression

Modulation of expression of a target nucleic acid can be achieved through alteration of any number of nucleic acid (DNA or RNA) functions. "Modulation" means a perturbation of function, for example, either an increase (stimulation or induction) or a decrease (inhibition or reduction) in expression. As another example, modulation of expression can include perturbing splice site selection of pre-mRNA processing. "Expression" includes all the functions by which a gene's coded information is converted into structures present and operating in a cell. These structures include the products of transcription and translation. "Modulation of expression" means the perturbation of such functions. The functions of DNA to be modulated can include replication and transcription. Replication and transcription, for example, can be from an endogenous cellular template, a vector, a plasmid construct or otherwise. The functions of RNA to be modulated can include translocation functions, which include, but are not limited to, translocation of the RNA to a site of protein translation, translocation of the RNA to sites within the cell which are distant from the site of RNA synthesis, and translation of protein from the RNA. RNA processing functions that can be modulated include, but are not limited to, splicing of the RNA to yield one or more RNA species, capping of the RNA, 3' maturation of the RNA and catalytic activity or complex formation involving the RNA which may be engaged in or facilitated by the RNA. Modulation of expression can result in the increased level of one or more nucleic acid species or the decreased level of one or more nucleic acid species, either temporally or by net steady state level. One result of such interference with target nucleic acid function is modulation of the expression of FR-alpha. Thus, in one embodiment modulation of expression can mean increase or decrease in target RNA or protein levels. In another embodiment modulation of expression can mean an increase or decrease of one or more RNA splice products, or a change in the ratio of two or more splice products.

The effect of the provided oligomeric compounds on target nucleic acid expression can be tested in any of a variety of cell types provided that the target nucleic acid is present at measurable levels. The effect of oligomeric compounds on target nucleic acid expression can be routinely determined using, for example, PCR or Northern blot analysis. Cell lines are derived from both normal tissues and cell types and from cells associated with various disorders (e.g. hyperproliferative disorders). Cell lines derived from multiple tissues and species can be obtained from American Type Culture Collection (ATCC, Manassas, Va.) and include: Caco-2, D1 TNC1, SKBR-3, SK-MEL-28, TRAMP-C1, U937, undifferentiated 3T3-L1, 7F2, 7D4, A375, ARIP, AML-12, A20, A549, A10, A431, BLO-11, BC3H1, B16-10, BW5147.3, BB88, BHK-21, BT-474, BEAS2B, C6, CMT-93, C3H/10T1/2, CHO-K1, ConA, C2C12, C3A, COS-7, CT26.WT, DDT1-MF2, DU145, D1B, E14, EMT-6, EL4, FAT7, GH1, GH3, G-361, HT-1080, HeLa, HCT116, H-4-II-E, HEK-293, HFN 36.3, HuVEC, HEPA1-6, H2.35, HK-2, Hep3B, HepG2, HuT 78, HL-60, H9c2(2-1), H9c2(2-1), IEC-6, IC21, JAR, JEG-3, Jurkat, K-562, K204, L2, LA4, LC-540, LLC1, LBRM-33, L6, LNcAP, LL2, MLg2908, MMT 060562, MH-S, MCF7, MDA MB231, MRC-5, M-3, Mia Paca, MLE12, MDA MB 468, MDA, NOR-10, NCTC 3749, N1S1, NBT-II, NIH/3T3, NCI-H292, NTERA-2 cl.D1, NIT-1, NCCIT, NR-8383, NRK, NG108-15, P388D1, PC-3, PANC-1, PC-12, P-19, P388D1 (IL-1), RFL-6, R2C, RK3E, Rin-M, Rin-5F, RBL-2H3, RMC, RAW264.7, Raji, Rat-2, SV40 MES 13, SMT/2A LNM, SW480, TCMK-1, THLE-3, TM-3, TM4, T3-3A1, T47D, T-24, THP-1, UMR-106, U-87 MG, U-2OS, VERO C1008, WISH, WEHI 231, Y-1, YB2/0, Y13-238, Y13-259, Yac-1, b.END, mIMCD-3, sw872 and 70Z3. Additional cell lines, such as HuH-7 and U373, can be obtained from the Japanese Cancer Research Resources Bank (Tokyo, Japan) and the Centre for Applied Microbiology and Research (Wiltshire, United Kingdom), respectively.

Primary cells, or those cells which are isolated from an animal and not subjected to continuous culture, can be prepared according to methods known in the art or obtained from various commercial suppliers. Additionally, primary cells include those obtained from donor human subjects in a clinical setting (i.e. blood donors, surgical patients). Primary cells prepared by methods known in the art include: mouse or rat bronchoalveolar lavage cells, mouse primary bone marrow-derived osteoclasts, mouse primary keratinocytes, human primary macrophages, mouse peritoneal macrophages, rat peritoneal macrophages, rat primary neurons, mouse primary osteoblasts, rat primary osteoblasts, rat cerebellum tissue cells, rat cerebrum tissue cells, rat hippocampal tissue cells, mouse primary splenocytes, human synoviocytes, mouse synoviocytes and rat synoviocytes. Additional types of primary cells, including human primary melanocytes, human primary monocytes, NHDC, NHDF, adult NHEK, neonatal NHEK, human primary renal proximal tubule epithelial cells, mouse embryonic fibroblasts, differentiated adipocytes, HASMC, HMEC, HMVEC-L, adult HMVEC-D, neonatal HMVEC-D, HPAEC, human primary hepatocytes, monkey primary hepatocytes, mouse primary hepatocytes, hamster primary hepatocytes, rabbit primary hepatocytes and rat primary hepatocytes, can be obtained from commercial suppliers such as Stem Cell Technologies; Zen-Bio, Inc. (Research Triangle Park, N.C.); Cambrex Biosciences (Walkersville, Md.); In Vitro Technologies (Baltimore, Md.); Cascade Biologics (Portland, Oreg.); Advanced Biotechnologies (Columbia, Md.).

Assaying Modulation of Expression

Modulation of FR-alpha expression can be assayed in a variety of ways known in the art. FR-alpha mRNA levels can be quantitated by, e.g., Northern blot analysis, competitive polymerase chain reaction (PCR), or real-time PCR. RNA analysis can be performed on total cellular RNA or poly(A)+ mRNA by methods known in the art. Methods of RNA isolation are taught in, for example, Ausubel, F. M. et al., *Current Protocols in Molecular Biology*, Volume 1, pp. 4.1.1-4.2.9 and 4.5.1-4.5.3, John Wiley & Sons, Inc., 1993.

Northern blot analysis is routine in the art and is taught in, for example, Ausubel, F. M. et al., *Current Protocols in Molecular Biology*, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Levels of a protein encoded by FR-alpha can be quantitated in a variety of ways well known in the art, such as immunoprecipitation, Western blot analysis (immunoblotting), ELISA or fluorescence-activated cell sorting (FACS). Antibodies directed to a protein encoded by FR-alpha can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., Current Protocols in Molecular Biology, Volume 2, pp. 11.12.1-11.12.9, John Wiley & Sons, Inc., 1997. Preparation of monoclonal antibodies is taught in, for example, Ausubel, F. M. et al., Current Protocols in Molecular Biology, Volume 2, pp. 11.4.1-11.11.5, John Wiley & Sons, Inc., 1997.

Immunoprecipitation methods are standard in the art and can be found at, for example, Ausubel, F. M. et al., Current Protocols in Molecular Biology, Volume 2, pp. 10.16.1-10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., Current Protocols in Molecular Biology, Volume 2, pp. 11.2.1-11.2.22, John Wiley & Sons, Inc., 1991.

Suitable Target Regions

Once one or more target regions, segments or sites have been identified, oligomeric compounds are designed which are sufficiently complementary to the target, i.e., hybridize sufficiently well and with sufficient specificity, to give the desired effect.

The oligomeric compounds can be targeted to features of a target nucleobase sequence, such as those described in Table 1. All regions of a nucleobase sequence to which an oligomeric compound can be targeted, wherein the regions are greater than or equal to 8 and less than or equal to 80 nucleobases, are described as follows:

Let $R(n, n+m-1)$ be a region from a target nucleobase sequence, where "n" is the 5'-most nucleobase position of the region, where "n+m-1" is the 3'-most nucleobase position of the region and where "m" is the length of the region. A set "S(m)", of regions of length "m" is defined as the regions where n ranges from 1 to L−m+1, where L is the length of the target nucleobase sequence and L>m. A set, "A", of all regions can be constructed as a union of the sets of regions for each length from where m is greater than or equal to 8 and is less than or equal to 80.

This set of regions can be represented using the following mathematical notation:

$$A = \bigcup_m S(m) \text{ where } m \in N \mid 8 \leq m \leq 80$$

and $$S(m) = \{R_{n,n+m-1} \mid n \in \{1, 2, 3, \ldots, L-m+1\}\}$$

where the mathematical operator | indicates "such that",
where the mathematical operator $\epsilon$ indicates "a member of a set" (e.g. y∈Z indicates that element y is a member of set Z),
where x is a variable,
where N indicates all natural numbers, defined as positive integers,
and where the mathematical operator $\bigcup$ indicates "the union of sets".

For example, the set of regions for m equal to 8, 20 and 80 can be constructed in the following manner. The set of regions, each 8 nucleobases in length, S(m=8), in a target nucleobase sequence 100 nucleobases in length (L=100), beginning at position 1 (n=1) of the target nucleobase sequence, can be created using the following expression:

$$S(8) = \{R_{1,8} \mid n \in \{1, 2, 3, \ldots, 93\}\}$$

and describes the set of regions comprising nucleobases 1-8, 2-9, 3-10, 4-11, 5-12, 6-13, 7-14, 8-15, 9-16, 10-17, 11-18, 12-19, 13-20, 14-21, 15-22, 16-23, 17-24, 18-25, 19-26, 20-27, 21-28, 22-29, 23-30, 24-31, 25-32, 26-33, 27-34, 28-35, 29-36, 30-37, 31-38, 32-39, 33-40, 34-41, 35-42, 36-43, 37-44, 38-45, 39-46, 40-47, 41-48, 42-49, 43-50, 44-51, 45-52, 46-53, 47-54, 48-55, 49-56, 50-57, 51-58, 52-59, 53-60, 54-61, 55-62, 56-63, 57-64, 58-65, 59-66, 60-67, 61-68, 62-69, 63-70, 64-71, 65-72, 66-73, 67-74, 68-75, 69-76, 70-77, 71-78, 72-79, 73-80, 74-81, 75-82, 76-83, 77-84, 78-85, 79-86, 80-87, 81-88, 82-89, 83-90, 84-91, 85-92, 86-93, 87-94, 88-95, 89-96, 90-97, 91-98, 92-99, 93-100.

An additional set for regions 20 nucleobases in length, in a target sequence 100 nucleobases in length, beginning at position 1 of the target nucleobase sequence, can be described using the following expression:

$$S(20) = \{R_{1,20} \mid n \in \{1, 2, 3, \ldots, 81\}\}$$

and describes the set of regions comprising nucleobases 1-20, 2-21, 3-22, 4-23, 5-24, 6-25, 7-26, 8-27, 9-28, 10-29, 11-30, 12-31, 13-32, 14-33, 15-34, 16-35, 17-36, 18-37, 19-38, 20-39, 21-40, 22-41, 23-42, 24-43, 25-44, 26-45, 27-46, 28-47, 29-48, 30-49, 31-50, 32-51, 33-52, 34-53, 35-54, 36-55, 37-56, 38-57, 39-58, 40-59, 41-60, 42-61, 43-62, 44-63, 45-64, 46-65, 47-66, 48-67, 49-68, 50-69, 51-70, 52-71, 53-72, 54-73, 55-74, 56-75, 57-76, 58-77, 59-78, 60-79, 61-80, 62-81, 63-82, 64-83, 65-84, 66-85, 67-86, 68-87, 69-88, 70-89, 71-90, 72-91, 73-92, 74-93, 75-94, 76-95, 77-96, 78-97, 79-98, 80-99, 81-100.

An additional set for regions 80 nucleobases in length, in a target sequence 100 nucleobases in length, beginning at position 1 of the target nucleobase sequence, can be described using the following expression:

$$S(80) = \{R_{1,80} \mid n \in \{1, 2, 3, \ldots, 21\}\}$$

and describes the set of regions comprising nucleobases 1-80, 2-81, 3-82, 4-83, 5-84, 6-85, 7-86, 8-87, 9-88, 10-89, 11-90, 12-91, 13-92, 14-93, 15-94, 16-95, 17-96, 18-97, 19-98, 20-99, 21-100.

Thus, in this example, A would include regions 1-8, 2-9, 3-10 . . . 93-100, 1-20, 2-21, 3-22 . . . 81-100, 1-80, 2-81, 3-82 . . . 21-100.

The union of these aforementioned example sets and other sets for lengths from 10 to 19 and 21 to 79 can be described using the mathematical expression $$A = \bigcup_m S(m)$$

where $\bigcup$ represents the union of the sets obtained by combining all members of all sets.

The mathematical expressions described herein defines all possible target regions in a target nucleobase sequence of any length L, where the region is of length m, and where m is greater than or equal to 8 and less than or equal to 80 nucleobases and, and where m is less than L, and where n is less than L−m+1.

Validated Target Segments

The locations on the target nucleic acid to which active oligomeric compounds hybridize are hereinbelow referred to as "validated target segments." As used herein the term "validated target segment" is defined as at least an 8-nucleobase portion of a target region to which an active oligomeric compound is targeted. While not wishing to be bound by theory, it is presently believed that these target segments represent portions of the target nucleic acid which are accessible for hybridization.

Target segments can include DNA or RNA sequences that comprise at least the 8 consecutive nucleobases from the 5'-terminus of a validated target segment (the remaining nucleobases being a consecutive stretch of the same DNA or RNA beginning immediately upstream of the 5'-terminus of the target segment and continuing until the DNA or RNA contains about 8 to about 80, or about 13 to about 80, or about 12 to about 50, or about 12 to about 30, or about 15 to about 30, or about 20 to about 30, or about 20 to about 24, or about 16 to about 20 nucleobases). Similarly validated target segments are represented by DNA or RNA sequences that comprise at least the 8 consecutive nucleobases from the 3'-terminus of a validated target segment (the remaining nucleobases being a consecutive stretch of the same DNA or RNA beginning immediately downstream of the 3'-terminus of the target segment and continuing until the DNA or RNA contains about 8 to about 80, or about 13 to about 80, or about 12 to about 50, or about 12 to about 30, or about 15 to about 30, or about 20 to about 30, or about 20 to about 24, or about 16 to about 20 nucleobases). It is also understood that a validated oligomeric target segment can be represented by DNA or RNA sequences that comprise at least 8 consecutive nucleobases from an internal portion of the sequence of a validated target segment, and can extend in either or both directions until the oligonucleotide contains about 8 to about 80, or about 13 to about 80, or about 12 to about 50, or about 12 to about 30, or about 15 to about 30, or about 20 to about 30, or about 20 to about 24, or about 16 to about 20 nucleobases.

Screening for Modulator Compounds

In another embodiment, the validated target segments identified herein can be employed in a screen for additional compounds that modulate the expression of FR-alpha. "Modulators" are those compounds that modulate the expression of FR-alpha and which comprise at least an 8-nucleobase portion which is complementary to a validated target segment. The screening method comprises the steps of contacting a validated target segment of a nucleic acid molecule encoding FR-alpha with one or more candidate modulators, and selecting for one or more candidate modulators which perturb the expression of a nucleic acid molecule encoding FR-alpha. Once it is shown that the candidate modulator or modulators are capable of modulating the expression of a nucleic acid molecule encoding FR-alpha, the modulator can then be employed in further investigative studies of the function of FR-alpha, or for use as a research, diagnostic, or therapeutic agent. The validated target segments can also be combined with a second strand as disclosed herein to form stabilized double-stranded (duplexed) oligonucleotides for use as a research, diagnostic, or therapeutic agent.

Kits, Research Reagents, Diagnostics, and Therapeutics

The oligomeric compounds can be utilized for diagnostics, therapeutics, prophylaxis and as research reagents and kits. Furthermore, antisense compounds, which are able to inhibit gene expression with specificity, are often used by those of ordinary skill to elucidate the function of particular genes or to distinguish between functions of various members of a biological pathway.

For use in kits and diagnostics, the oligomeric compounds, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more compounds or compositions are compared to control cells or tissues not treated with compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A.*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

Compounds provided herein can be used to modulate the expression of FR-alpha in an animal, such as a human. In one non-limiting embodiment, the methods comprise the step of administering to said animal an effective amount of an antisense compound that inhibits expression of FR-alpha. In one embodiment, the antisense compounds effectively inhibit the levels or function of FR-alpha RNA. Because reduction in FR-alpha mRNA levels can lead to alteration in FR-alpha protein products of expression as well, such resultant alterations can also be measured. Antisense compounds that effectively inhibit the levels or function of FR-alpha RNA or protein products of expression is considered an active antisense compound. In one embodiment, the antisense compounds inhibit the expression of FR-alpha causing a reduction of RNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of FR-alpha can be measured in a bodily fluid, tissue or organ of the animal. Bodily fluids include, but are not limited to, blood (serum or plasma), lymphatic fluid, cerebrospinal fluid, semen, urine, synovial fluid and saliva and can be obtained by methods routine to those skilled in the art. Tissues or organs include, but are not limited to, blood (e.g., hematopoietic cells, such as human hematopoietic progenitor cells, human hematopoietic stem cells, CD34+ cells CD4+ cells), lymphocytes and other blood lineage cells, skin, bone marrow, spleen, thymus, lymph node, brain, spinal cord, heart, skeletal muscle, liver, pancreas, prostate, kidney, lung, oral mucosa, esophagus, stomach, ilium, small intestine, colon, bladder, cervix, ovary, testis, mammary gland, adrenal gland, and adipose (white and brown). Samples of tissues or organs can be routinely obtained by biopsy. In some alternative situations, samples of tissues or organs can be recovered from an animal after death.

The cells contained within said fluids, tissues or organs being analyzed can contain a nucleic acid molecule encoding FR-alpha protein and/or the FR-alpha-encoded protein itself. For example, fluids, tissues or organs procured from an animal can be evaluated for expression levels of the target mRNA or protein. mRNA levels can be measured or evaluated by real-time PCR, Northern blot, in situ hybridization or DNA array analysis. Protein levels can be measured or evaluated by ELISA, immunoblotting, quantitative protein assays, protein activity assays (for example, caspase activity assays) immunohistochemistry or immunocytochemistry. Furthermore, the effects of treatment can be assessed by measuring biomarkers associated with the target gene expression in the aforementioned fluids, tissues or organs, collected from an animal contacted with one or more compounds, by routine clinical methods known in the art. These biomarkers include but are not limited to: glucose, cholesterol, lipoproteins, triglycerides, free fatty acids and other markers of glucose and lipid metabolism; liver transaminases, bilirubin, albumin, blood urea nitrogen, creatine and other markers of kidney and liver function; interleukins, tumor necrosis factors, intracellular adhesion molecules, C-reactive protein and other markers of inflammation; testosterone, estrogen and other hormones; tumor markers; vitamins, minerals and electrolytes.

The compounds provided herein can be utilized in pharmaceutical compositions by adding an effective amount of a compound to a suitable pharmaceutically acceptable diluent or carrier. In one aspect, the compounds inhibit the expression of FR-alpha. The compounds can also be used in the manufacture of a medicament for the treatment of diseases and disorders related to FR-alpha expression.

Methods whereby bodily fluids, organs or tissues are contacted with an effective amount of one or more of the antisense compounds or compositions are also contemplated. Bodily fluids, organs or tissues can be contacted with one or more of the compounds resulting in modulation of FR-alpha expression in the cells of bodily fluids, organs or tissues. An effective amount can be determined by monitoring the modulatory effect of the antisense compound or compounds or compositions on target nucleic acids or their products by methods routine to the skilled artisan. Further contemplated are ex vivo methods of treatment whereby cells or tissues are isolated from a subject, contacted with an effective amount of the antisense compound or compounds or compositions and reintroduced into the subject by routine methods known to those skilled in the art.

In one embodiment, provided are uses of a compound of an isolated double stranded RNA oligonucleotide in the manufacture of a medicament for inhibiting FR-alpha expression or overexpression. Thus, provided herein is the use of an isolated double stranded RNA oligonucleotide targeted to FR-alpha in the manufacture of a medicament for the treatment of a disease or disorder by means of the method described above.

Salts, Prodrugs and Bioequivalents

The oligomeric compounds comprise any pharmaceutically acceptable salts, esters, or salts of such esters, or any other functional chemical equivalent which, upon administration to an animal including a human, is capable of providing (directly or indirectly) the biologically active metabolite or residue thereof. Accordingly, for example, the disclosure is also drawn to prodrugs and pharmaceutically acceptable salts of the oligomeric compounds, pharmaceutically acceptable salts of such prodrugs, and other bioequivalents.

The term "prodrug" indicates a therapeutic agent that is prepared in an inactive or less active form that is converted to an active form (i.e., drug) within the body or cells thereof by the action of endogenous enzymes or other chemicals and/or conditions. In particular, prodrug versions of the oligonucleotides are prepared as SATE ((S-acetyl-2-thioethyl)phosphate) derivatives according to the methods disclosed in WO 93/24510 or WO 94/26764.

The term "pharmaceutically acceptable salts" refers to physiologically and pharmaceutically acceptable salts of the compounds: i.e., salts that retain the desired biological activity of the parent compound and do not impart undesired toxicological effects thereto.

Formulations

The oligomeric compounds provided herein may also be formulated with active or inert ingredients, or a combination of both, for delivery via parenteral and non-parenteral routes of administration. Compositions and methods of preparing formulations are well known to those skilled in the art.

Nonlimiting Disclosure and Incorporation by Reference

While certain compounds, compositions and methods have been described with specificity in accordance with certain embodiments, the following examples serve only to illustrate the compounds provided herein and are not intended to limit the same. Each of the references, GENBANK® accession numbers, and the like recited in the present application is incorporated herein by reference in its entirety.

Example 1

The effect of oligomeric compounds on target nucleic acid expression was tested in HeLa cells. The human epithelioid carcinoma cell line HeLa was obtained from the American Tissue Type Culture Collection (Manassas, Va.). HeLa cells were routinely cultured in DMEM, high glucose (Invitrogen Life Technologies, Carlsbad, Calif.) supplemented with 10% fetal bovine serum (Invitrogen Life Technologies, Carlsbad, Calif.). Cells were routinely passaged by trypsinization and dilution when they reached 90% confluence. Cells were seeded into 24-well plates (Falcon-Primaria #3846) at a density of 50,000 cells/well or in 96-well plates at a density of 5,000 cells/well for use in RT-PCR analysis. When cells reached appropriate confluency, they were treated with oligonucleotide using Lipofectin™ as described.

Oligonucleotide was mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of oligonucleotide and a LIPOFECTIN™ concentration of 2.5 or 3

µg/mL per 100 nM oligonucleotide. This transfection mixture was incubated at room temperature for approximately 0.5 hours. For cells grown in 96-well plates, wells were washed once with 100 µL OPTI-MEM™-1 and then treated with 130 µL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture was replaced with fresh culture medium. Cells were harvested 16-24 hours after oligonucleotide treatment.

Control oligonucleotides are used to determine the optimal oligomeric compound concentration for a particular cell line. Furthermore, when oligomeric compounds are tested in oligomeric compound screening experiments or phenotypic assays, control oligonucleotides are tested in parallel. The concentration of oligonucleotide used varies from cell line to cell line.

Example 2

Real-Time Quantitative PCR Analysis of FR-Alpha mRNA Levels

Quantitation of FR-alpha mRNA levels was accomplished by real-time quantitative PCR using the ABI PRISM™ 7600, 7700, or 7900 Sequence Detection System (PE-Applied Biosystems, Foster City, Calif.) according to manufacturer's instructions.

Prior to quantitative PCR analysis, primer-probe sets specific to the target gene being measured were evaluated for their ability to be "multiplexed" with a GAPDH amplification reaction. After isolation the RNA is subjected to sequential reverse transcriptase (RT) reaction and real-time PCR, both of which are performed in the same well. RT and PCR reagents were obtained from Invitrogen Life Technologies (Carlsbad, Calif.). RT, real-time PCR was carried out in the same by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by RT, real-time PCR were normalized using either the expression level of GAPDH, a gene whose expression is constant, or by quantifying total RNA using RiboGreen™ (Molecular Probes, Inc. Eugene, Oreg.). GAPDH expression was quantified by RT, real-time PCR, by being run simultaneously with the target, multiplexing, or separately. Total RNA was quantified using RiboGreen™ RNA quantification reagent (Molecular Probes, Inc. Eugene, Oreg.).

170 µL of RiboGreen™ working reagent (RiboGreen™ reagent diluted 1:350 in 10 mM Tris-HCl, 1 mM EDTA, pH 7.5) was pipetted into a 96-well plate containing 30 µL purified cellular RNA. The plate was read in a CytoFluor 4000 (PE Applied Biosystems) with excitation at 485 nm and emission at 530 nm.

Probes and primers for use in real-time PCR were designed to hybridize to target-specific sequences (Table 2). The target-specific PCR probes have FAM covalently linked to the 5' end and TAMRA or MGB covalently linked to the 3' end, where FAM is the fluorescent dye and TAMRA or MGB is the quencher dye.

TABLE 2

FR-alpha specific primers and probes for use in real-time PCR

| Sequence Description | Sequence (5' to 3') | SEQ ID NO |
|---|---|---|
| Forward Primer | GAAATCCCTGCCCTGTTCAG | 8 |
| Reverse Primer | AGAGGCCCGACCATGGA | 9 |
| Probe | AGCTCCCAACTATTTG | 10 |

Example 3

Antisense Inhibition of FR-Alpha by Oligomeric Compounds

A series of oligomeric compounds was designed to target different regions of FR-alpha using published sequences cited in Table 1. The compounds are shown in Table 3. All compounds in Table 3 are chimeric oligonucleotides ("gapmers") 20 nucleotides in length, composed of a central "gap" region consisting of 10 2'-deoxynucleotides, which is flanked on both sides (5' and 3') by five-nucleotide "wings". The wings are composed of 2'-O-(2-methoxyethyl) nucleotides, also known as 2'-MOE nucleotides. The internucleoside (backbone) linkages are phosphorothioate throughout the oligonucleotide. All cytidine residues are 5-methylcytidines. HeLa cells were transfected with 50 nM of each compound and the compounds were analyzed for their effect on FR-alpha mRNA levels by quantitative real-time PCR as described in other examples herein. Data are averages from experiments in which cultured cells were treated with the disclosed oligomeric compounds. Shown in Table 3 is the SEQ ID NO of the sequence to which each oligomeric compound is targeted.

A reduction in expression is expressed as percent inhibition. If the target expression level of oligomeric compound-treated cell was higher than control, percent inhibition is expressed as zero inhibition. The target regions to which these oligomeric compounds are inhibitory are herein referred to as "validated target segments."

TABLE 3

Inhibition of gene target mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 390936 | 1 | 918 | ATTCTCAAGACACATGTGCG | 35 | 11 |
| 390937 | 2 | 51 | CAGTTCCTGGGAGAGGAGGT | 0 | 12 |
| 390938 | 2 | 69 | CAGGTGATCCTTTGGGTTCA | 0 | 13 |
| 390939 | 2 | 75 | GAATACCAGGTGATCCTTTG | 0 | 14 |
| 390940 | 2 | 80 | TCAGGGAATACCAGGTGATC | 0 | 15 |
| 390941 | 2 | 85 | TACTCTCAGGGAATACCAGG | 0 | 16 |
| 390942 | 2 | 106 | GGGCCACGCCGGAGAAATCT | 2 | 17 |
| 390943 | 2 | 140 | TGTTGTCATCCGCTGAGCCA | 60 | 18 |
| 390944 | 2 | 163 | CACACTAGAAGGAGCAGCAG | 65 | 19 |
| 390945 | 2 | 176 | TACTACAGCCACCCACACTA | 42 | 20 |

TABLE 3-continued

Inhibition of gene target mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 390946 | 2 | 202 | CATGCAATCCTTGTCTGAGC | 62 | 21 |
| 390947 | 2 | 213 | CAGTCCTGGCCCATGCAATC | 53 | 22 |
| 390948 | 2 | 294 | GTCGACACTGCTCATGCAAC | 43 | 23 |
| 390949 | 2 | 300 | TCCAGGGTCGACACTGCTCA | 71 | 24 |
| 390950 | 2 | 366 | TATATAGGTAGGAAACATCC | 45 | 25 |
| 390951 | 2 | 369 | ATCTATATAGGTAGGAAACA | 21 | 26 |
| 390952 | 2 | 581 | GCTCTTGCAGGTGTAGGAGG | 48 | 27 |
| 390953 | 2 | 633 | CCACTGCGCACTTGTTAAAC | 43 | 28 |
| 390954 | 2 | 899 | AGGAGGTCAGCTGAGCAGCC | 46 | 29 |
| 390955 | 2 | 906 | AGGTAAAAGGAGGTCAGCTG | 42 | 30 |
| 390956 | 2 | 912 | ATCAGAAGGTAAAAGGAGGT | 29 | 31 |
| 390957 | 2 | 929 | GGCAGGGATTTCCAGGTATC | 88 | 32 |
| 390958 | 2 | 964 | GGAACCAAATAGTTGGGAGC | 81 | 33 |
| 390959 | 2 | 973 | CATGGAGCAGGAACCAAATA | 68 | 34 |
| 390960 | 2 | 986 | TCAGAGGCCCGACCATGGAG | 84 | 35 |
| 390961 | 2 | 1006 | TGGTTTATTCAAAGTGGCTG | 92 | 36 |
| 390962 | 2 | 1011 | GTGTCTGGTTTATTCAAAGT | 89 | 37 |
| 390963 | 3 | 8 | TGTATGTGAGCACCAGCCAG | 0 | 38 |
| 390964 | 3 | 40 | GATTGGGCGAAGGCCACTCA | 0 | 39 |
| 390965 | 3 | 89 | CCTAGGAGACAGGCAGGGAG | 0 | 40 |
| 390966 | 3 | 128 | CCCCTTGCCTTATTCCAGGG | 0 | 41 |
| 390967 | 4 | 3 | TGGTCAGTGGCACCAAGGAA | 5 | 42 |
| 390968 | 4 | 23 | TGTCCCTGAAGAAAGAGCTG | 37 | 43 |
| 390969 | 5 | 1 | GGGCTGAGAAAATCCTTTCC | 0 | 44 |
| 390970 | 5 | 28 | GCGGCCAACACACAGTGCTG | 0 | 45 |
| 390971 | 5 | 43 | GAGGCTCTCATGGGTGCGGC | 2 | 46 |
| 390972 | 5 | 58 | CACCTTCAGAGTGCTGAGGC | 0 | 47 |
| 390973 | 5 | 90 | CAGGCCAGAGCTCTTTTGGC | 0 | 48 |
| 390974 | 5 | 105 | GGGACCACCCAAGTTCAGGC | 3 | 49 |
| 390975 | 5 | 110 | CAGTAGGGACCACCCAAGTT | 0 | 50 |
| 390976 | 5 | 125 | ATGCCCCAAGTCACACAGTA | 0 | 51 |
| 390977 | 5 | 140 | GCACAGATGAGGGCCATGCC | 0 | 52 |
| 390978 | 5 | 146 | ATTTCAGCACAGATGAGGGC | 0 | 53 |
| 390979 | 5 | 157 | TTTGTGGAATCATTTCAGCA | 0 | 54 |
| 390980 | 5 | 168 | CCAGTTTAATCTTTGTGGAA | 0 | 55 |
| 390981 | 5 | 180 | AACAAATGATAGCCAGTTTA | 3 | 56 |
| 390982 | 5 | 211 | TGCAAGGATTAAATGTAAGA | 0 | 57 |
| 390983 | 5 | 246 | AGAGAAGCAAACTATCTTGA | 0 | 58 |
| 390984 | 5 | 316 | AGCACAGGGTTCCCGTTCAA | 0 | 59 |
| 390985 | 5 | 323 | TGTTTAGAGCACAGGGTTCC | 0 | 60 |
| 390986 | 5 | 350 | TCAGTTCCTGCGGGAACAAA | 0 | 61 |
| 390987 | 7 | 1547 | GAGTGTCACATACCTGGGAG | 0 | 62 |
| 390988 | 7 | 1637 | TTCAGGCAAACAGAGGGCCC | 0 | 63 |
| 390989 | 7 | 1720 | GGATGAACACTAACTTGTCG | 0 | 64 |
| 390990 | 7 | 2423 | CACTAACCTTGAGGGCCACG | 0 | 65 |
| 390991 | 7 | 2503 | TGATTCCAGTGTTCATTCAC | 0 | 66 |
| 390992 | 7 | 2816 | GACACCAGGTGTCTGGGCCC | 0 | 67 |
| 390993 | 7 | 3496 | ATTAATTTTCAGGTCAGATT | 11 | 68 |
| 390994 | 7 | 3540 | ACAGTTACACTAGTGGGATA | 8 | 69 |
| 390995 | 7 | 3573 | TACCCAATAATCAAGTGTAT | 3 | 70 |
| 390996 | 7 | 3620 | TTTTAGGATTTCATCAAAGG | 0 | 71 |
| 390997 | 7 | 3662 | TAGGTCCACAATGCCTTATT | 0 | 72 |
| 390998 | 7 | 3671 | AGTTTGCCATAGGTCCACAA | 0 | 73 |
| 390999 | 7 | 3700 | GATTTGGGCAAAATGCAGAA | 0 | 74 |
| 391000 | 7 | 3718 | TGATATAATTCAAGGATGGA | 4 | 75 |
| 391001 | 7 | 3795 | AATGAAAGGTAGGATTAGAC | 0 | 76 |
| 391002 | 7 | 4210 | TCAGTTCACCAGTGAATGGG | 40 | 77 |
| 391003 | 7 | 4430 | TTTGGAGGAGTCATTCCCAG | 36 | 78 |
| 391004 | 7 | 4737 | ACCTCAGGTCCAATGTGGTC | 7 | 79 |
| 391005 | 7 | 4759 | GCAAAATAAATGTTATAGGG | 7 | 80 |
| 391006 | 7 | 4797 | AGTTATATCATCATGTTCAG | 33 | 81 |
| 391007 | 7 | 6050 | CCAATCAATTGTGGATGTTA | 44 | 82 |
| 391008 | 7 | 6630 | GCAATTTAAATTGTAACCCC | 31 | 83 |
| 391009 | 7 | 6833 | TACAAAATTTGTTAATTCAA | 6 | 84 |
| 391010 | 7 | 7253 | TGCAGGAAGCCATGCATACC | 12 | 85 |
| 391011 | 7 | 7358 | TCAGGTTCAAGAATCCCAGC | 8 | 86 |
| 391012 | 7 | 7368 | AAAGAAGGGCTCAGGTTCAA | 0 | 87 |
| 391013 | 7 | 7389 | CACCTGGGTGATTTTGATAC | 0 | 88 |

As shown in Table 4, SEQ ID NOs 11, 18-37, 43, 68, 77, 78, 81-83 and 85 inhibited expression of FR-alpha mRNA by at least 10%; SEQ ID NOs 11, 18-25, 27-30, 32-37, 43 and 81-83 inhibited expression of FR-alpha mRNA by at least 30%; and SEQ ID NOs 18, 19, 21, 24 and 32-37 inhibited expression of FR-alpha mRNA by at least 60%.

Example 4

Design and Screening of Duplexed Oligomeric Compounds Targeting FR-Alpha

A series of duplexes, including dsRNA and mimetics thereof, comprising the compounds provided herein and their complements can be designed to target FR-alpha. The nucleobase sequence of the antisense strand of the duplex comprises at least a portion of an antisense oligonucleotide targeted to FR-alpha as described herein. The ends of the strands may be modified by the addition of one or more natural or modified nucleobases to form an overhang. The sense strand of the dsRNA is then designed and synthesized as the complement of the antisense strand and may also contain modifications or additions to either terminus. The antisense and sense strands of the duplex comprise from about 17 to 25 nucleotides or from about 19 to 23 nucleotides. Alternatively, the antisense and sense strands comprise 20, 21, or 22 nucleotides.

For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (SEQ ID NO: 89) and having a two-nucleobase overhang of deoxythymidine (dT) would have the following structure:

```
cgagaggcggacgggaccgTT   Antisense Strand (SEQ ID NO: 90)
|||||||||||||||||||
TTgcucuccgccugcccuggc         Complement (SEQ ID NO: 91)
```

Overhangs can range from 2 to 6 nucleobases and these nucleobases may or may not be complementary to the target nucleic acid. In another embodiment, the duplexes can have an overhang on only one terminus.

In another embodiment, a duplex comprising an antisense strand having the same sequence CGAGAGGCGGACGG-GACCG (SEQ ID NO: 89) may be prepared with blunt ends (no single stranded overhang) as shown:

```
cgagaggcggacgggaccg   Antisense Strand (SEQ ID NO: 89)
|||||||||||||||||||
gcucuccgccugcccuggc         Complement (SEQ ID NO: 92)
```

The RNA duplex can be unimolecular or bimolecular; i.e., the two strands can be part of a single molecule or may be separate molecules.

RNA strands of the duplex can be synthesized by methods routine to the skilled artisan or purchased from Dharmacon Research Inc., (Lafayette, Colo.). Once synthesized, the complementary strands are annealed. The single strands are aliquotted and diluted to a concentration of 50 µM. Once diluted, 30 µL of each strand is combined with 15 µL of a 5× solution of annealing buffer. The final concentration of said buffer is 100 mM potassium acetate, 30 mM HEPES-KOH pH 7.4, and 2 mM magnesium acetate. The final volume is 75 µL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 µM.

Once prepared, the duplexed compounds are evaluated for their ability to modulate target mRNA levels When cells reach 80% confluency, they are treated with duplexed compounds. For cells grown in 96-well plates, wells are washed once with 200 µL OPTI-MEM® 1 reduced-serum medium (Invitrogen Life Technologies, Carlsbad, Calif.) and then treated with 130 µL of OPTI-MEM® 1 containing 5 µg/mL LIPO-FECTAMINE 2000™ (Invitrogen Life Technologies, Carlsbad, Calif.) and the duplex antisense compound at the desired final concentration. After about 4 hours of treatment, the medium is replaced with fresh medium. Cells are harvested 16 hours after treatment, at which time RNA is isolated and target reduction measured by quantitative real-time PCR as described herein.

What is claimed is:

1. A compound comprising a modified oligonucleotide consisting of 12 to 50 linked nucleosides targeted to a nucleic acid molecule encoding FR-alpha, wherein said modified oligonucleotide has a nucleobase sequence comprising at least 8 consecutive nucleotides complementary within nucleotides 964-1030 of SEQ ID NO:2, wherein said modified oligonucleotide has a nucleobase sequence comprising at least 8 consecutive nucleobases of a nucleobase sequence selected from the group consisting of SEQ ID NO: 33, 34, 35, 36, and 37, wherein said nucleobase sequence of said modified oligonucleotide is at least 90% complementary to SEQ ID NO:2 as measured over the entirety of said nucleobase sequence of said modified oligonucleotide, wherein the modified oligonucleotide comprises:
   a gap segment consisting of linked deoxynucleosides;
   a 5' wing segment consisting of linked nucleosides;
   a 3' wing segment consisting of linked nucleosides;
   wherein the gap segment is positioned between the 5' wing segment and the 3' wing segment, wherein each nucleoside of each wing segment comprises a modified sugar, and wherein said compound inhibits the expression of FR-alpha.

2. The compound of claim 1, wherein the modified oligonucleotide comprises:
   a gap segment consisting often linked deoxynucleosides;
   a 5' wing segment consisting of five linked nucleosides;
   a 3' wing segment consisting of five linked nucleosides;
   wherein the gap segment is positioned between the 5' wing segment and the 3' wing segment, wherein each nucleoside of each wing segment comprises a 2'-O-methoxyethyl sugar; wherein each cytosine in said modified oligonucleotide is a 5-methylcytosine, and wherein each internucleoside linkage of said modified oligonucleotide is a phosphorothioate linkage.

3. The compound of claim 2, wherein the modified oligonucleotide consists of 20 linked nucleosides.

4. The compound of claim 3, wherein said modified oligonucleotide has a nucleobase sequence consisting of SEQ ID NO:33.

5. The compound of claim 3, wherein said modified oligonucleotide has a nucleobase sequence consisting of SEQ ID NO:34.

6. The compound of claim 3, wherein said modified oligonucleotide has a nucleobase sequence consisting of SEQ ID NO:35.

7. The compound of claim 3, wherein said modified oligonucleotide has a nucleobase sequence consisting of SEQ ID NO:36.

8. The compound of claim 3, wherein said modified oligonucleotide has a nucleobase sequence consisting of SEQ ID NO:37.

9. A composition comprising the compound of claim 1 or a salt thereof and a pharmaceutically acceptable carrier or diluent.

10. The composition of claim 9, wherein said compound consists of a single-stranded oligonucleotide.

11. The composition of claim 9, wherein the modified oligonucleotide consists of 20 linked nucleosides.

12. The compound of claim 1, consisting of a single stranded modified oligonucleotide.

13. The compound of claim 1, wherein said modified oligonucleotide consists of 12 to 30 linked nucleosides.

14. The compound of claim 1, wherein said modified oligonucleotide consists of 15 to 30 linked nucleosides.

15. The compound of claim 1, wherein the nucleobase sequence of said modified oligonucleotide is at least 95% complementary to SEQ ID NO:2 as measured over the entirety of said nucleobase sequence of said modified oligonucleotide.

16. The compound of claim 1, wherein the nucleobase sequence of said modified oligonucleotide is 100% complementary to SEQ ID NO:2 as measured over the entirety of said nucleobase sequence of said modified oligonucleotide.

17. A method of inhibiting the expression of FR-alpha in a bodily fluid, cell or tissue comprising contacting said bodily fluid, cell or tissue with the compound of claim 1 so that expression of FR-alpha is inhibited.

18. A method of treating a hyperproliferative disorder in a subject comprising administering to said subject the pharmaceutical composition of claim 9.

19. The method of claim 18 wherein said hyperproliferative disorder is ovarian, breast, brain, lung, or colorectal cancer.

20. A method of inhibiting infection by Marburg or Ebola viruses in a subject comprising administering to said subject the pharmaceutical composition of claim 9.

21. A compound comprising a modified oligonucleotide consisting of 12 to 50 linked nucleosides targeted to a nucleic acid molecule encoding FR-alpha, wherein said modified oligonucleotide has a nucleobase sequence comprising at least 8 consecutive nucleotides complementary within nucleotides 964-1030 of SEQ ID NO:2, wherein said nucleobase sequence of said modified oligonucleotide is at least 90% complementary to SEQ ID NO:2 as measured over the entirety of said nucleobase sequence of said modified oligonucleotide, wherein the modified oligonucleotide comprises:

a gap segment consisting of linked deoxynucleosides;
a 5' wing segment consisting of linked nucleosides;
a 3' wing segment consisting of linked nucleosides;
wherein the gap segment is positioned between the 5' wing segment and the 3' wing segment, wherein each nucleoside of each wing segment comprises a modified sugar, and wherein said compound inhibits the expression of FR-alpha.

22. The compound of claim 21, wherein the modified oligonucleotide comprises:

a gap segment consisting of ten linked deoxynucleosides;
a 5' wing segment consisting of five linked nucleosides;
a 3' wing segment consisting of five linked nucleosides;
wherein the gap segment is positioned between the 5' wing segment and the 3' wing segment, wherein each nucleoside of each wing segment comprises a methoxyethyl sugar; wherein each cytosine in said modified oligonucleotide is a 5-methylcytosine, and wherein each internucleoside linkage of said modified oligonucleotide is a phosphorothioate linkage.

23. The compound of claim 22, wherein the modified oligonucleotide consists of 20 linked nucleosides.

24. The compound of claim 23, wherein said modified oligonucleotide has a nucleobase sequence consisting of SEQ ID NO:33.

25. The compound of claim 23, wherein said modified oligonucleotide has a nucleobase sequence consisting of SEQ ID NO:34.

26. The compound of claim 23, wherein said modified oligonucleotide has a nucleobase sequence consisting of SEQ ID NO:35.

27. The compound of claim 23, wherein said modified oligonucleotide has a nucleobase sequence consisting of SEQ ID NO:36.

28. The compound of claim 23, wherein said modified oligonucleotide has a nucleobase sequence consisting of SEQ ID NO:37.

29. The compound of claim 21, consisting of a single stranded modified oligonucleotide.

30. The compound of claim 21, wherein said modified oligonucleotide consists of 12 to 30 linked nucleosides.

31. The compound of claim 21, wherein said modified oligonucleotide consists of 15 to 30 linked nucleosides.

32. The compound of claim 21, wherein the nucleobase sequence of said modified oligonucleotide is at least 95% complementary to SEQ ID NO:2 as measured over the entirety of said nucleobase sequence of said modified oligonucleotide.

33. The compound of claim 21, wherein the nucleobase sequence of said modified oligonucleotide is 100% complementary to SEQ ID NO:2 as measured over the entirety of said nucleobase sequence of said modified oligonucleotide.

34. A composition comprising the compound of claim 21 or a salt thereof and a pharmaceutically acceptable carrier or diluent.

35. The composition of claim 34, wherein said compound consists of a single-stranded oligonucleotide.

36. The composition of claim 34, wherein the modified oligonucleotide consists of 20 linked nucleosides.

37. A method of inhibiting the expression of FR-alpha in a bodily fluid, cell or tissue comprising contacting said bodily fluid, cell or tissue with the compound of claim 21 so that expression of FR-alpha is inhibited.

38. A method of treating a hyperproliferative disorder in a subject comprising administering to said subject the pharmaceutical composition of claim 34.

39. The method of claim 38 wherein said hyperproliferative disorder is ovarian, breast, brain, lung, or colorectal cancer.

40. A method of inhibiting infection by Marburg or Ebola viruses in a subject comprising administering to said subject the pharmaceutical composition of claim 21.

* * * * *